United States Patent
Hansson et al.

(10) Patent No.: US 10,035,821 B2
(45) Date of Patent: Jul. 31, 2018

(54) CALCIUM BINDING COMPOUNDS BASED ON GAMMA-CARBOXY GLUTAMATE

(71) Applicant: Gunnar C. Hansson, Göteborg (SE)

(72) Inventors: Gunnar C. Hansson, Göteborg (SE);
Anna Ermund, Västra Frölunda (SE);
Christian Recktenwald, Göteborg (SE)

(73) Assignee: Gunnar C. Hansson, Göteborg (SE)

( * ) Notice: Subject to any disclaimer, the term of this patent is extended or adjusted under 35 U.S.C. 154(b) by 0 days.

(21) Appl. No.: 15/299,557

(22) Filed: Oct. 21, 2016

(65) Prior Publication Data

US 2018/0111962 A1 Apr. 26, 2018

(51) Int. Cl.
*C07K 7/06* (2006.01)
*A61K 9/00* (2006.01)
*A61K 45/06* (2006.01)
*A61K 38/08* (2006.01)

(52) U.S. Cl.
CPC .............. *C07K 7/06* (2013.01); *A61K 9/0073* (2013.01); *A61K 38/08* (2013.01); *A61K 45/06* (2013.01)

(58) Field of Classification Search
CPC ........ C07K 7/06; A61K 9/0073; A61K 45/06; A61K 38/08
See application file for complete search history.

(56) References Cited

FOREIGN PATENT DOCUMENTS

| WO | 2006083126 A1 | 8/2006 |
|---|---|---|
| WO | 2010124058 A1 | 10/2010 |

OTHER PUBLICATIONS

Lin et al. Calcium binding mode of gamma-carboxyglutamic acids in conantokins, Protein Engineering, 12 (7), 589-595, 1999.*

Gustafsson, J.K. et al., Bicarbonate and functional CFTR channel is required for proper mucin secretion and link Cystic Fibrosis with its mucus phenotype, J. Exp. Med. (2012) 209:1263-1272.
Schütte, A. et al., Microbial Induced Meprin β Cleavage in MUC2 Mucin and Functional CFTR Channel are Required to Release Anchored Small Intestinal Mucus, Proc. Nat'l. Acad. Sci. USA (2014) 111:12396-12401.
Ambort, D. et al., Perspectives on Mucus Properties and Formation—Lessons from the Biochemical World, Cold Spring Harbor Perspectives in Medicine (2012) 2:a014159.
Gustafsson, J.K. et al., An ex vivo method for studying mucus formation, properties and thickness in human colonic biopsies and mouse small and large intestinal explants, Am. J. Physiol. (2012) 302:G430-G438.
Ermund, A. et al., Hypertonic saline releases the attached small intestinal cystic fibrosis mucus, Clin. Exp. Pharm. Physiol. (2015) 42, 69-75.
Ermund, A. et al., Hyper-osmolarity and calcium chelation: Effects on cystic fibrosis mucus, Eur J Pharmacol. (2015) 764: 109-117.
Colpitts, et al., Binding of calcium to synthetic peptides containing y-carboxyglutamic acid, Department of Chemisty and Biochemistry, University of Notre Dame, Jan. 1, 1993, pp. 567-275.
Prorok, Mary et al., Calcium Binding Properties of Synthetic y-Carboxyglutamic Acid-Containing . . . , Biochemistry American Chem. Society, vol. 35, No. 51, 1996, pp. 16528-16534.
Ermund, A. et al., Structure-activity relationship for OligoG-induced normalization for the CF mucus phenotype., Journal of Cystic Fibrosis, Elsevier, 2015, vol. 14, p. S37.
Donaldson, Scott H. et al., Mucus Clearance and Lung Function in Cystic Fibrosis with Hypertonic Saline, New England Journal of Medicine, Jan. 19, 2006, pp. 241-250.
Extended European Search Report dated Dec. 3, 2018 in EP Application No. 17196512.2.

* cited by examiner

*Primary Examiner* — Johann R Richter
*Assistant Examiner* — Genevieve S Alley
(74) *Attorney, Agent, or Firm* — Dilworth IP, LLC

(57) ABSTRACT

Compounds capable of binding calcium ions comprising a certain number of gamma-carboxy glutamate units have been found useful in treating and/or preventing mucus accumulation and stagnation in the respiratory tract. Pharmaceutical compositions comprising such compounds are disclosed. Such compounds and pharmaceutical compositions may be used for treatment of disorders of the respiratory tract.

8 Claims, 10 Drawing Sheets

CALCIUM BINDING COMPOUNDS BASED ON GAMMA-CARBOXY GLUTAMATE

FIELD OF THE INVENTION

The present invention relates to compounds and compositions useful in the treatment and/or prevention of a disorder characterized by mucus stagnation in the upper and/or lower respiratory tract.

BACKGROUND OF THE INVENTION

Today there are many people suffering from different types of disorders related to dysfunctions from the respiratory tract. Common examples are bronchitis, chronic bronchitis, chronic obstructive pulmonary disease (COPD), asthma, emphysema, cystic fibrosis (CF) and also common colds. Some of these diseases are chronic conditions and these have large negative impact on the life of the person.

These diseases can be caused by different mechanisms and generally give inflammation. Common to all these disorders are an increased production and accumulation of mucus in the lungs. In the chronic lung diseases the accumulated mucus often becomes colonized by bacteria, further worsening the disease problems.

Different methods of treatment of these disorders have been suggested to treat and/or reduce the symptoms of such disorders. Since most of these disorders are chronic conditions, the method of treatment may be long-term. As these diseases have bacterial colonization as a common denominator, antibiotics are commonly administered. However, in many situations this only lowers the bacterial number for the moment as the mucus remains in the lungs.

Mucus is a mixture of molecules where the large polymer forming mucins are a major constituent. This is MUC2 in the intestine and MUC5B and MUC5AC in the lungs. These molecules are stored in goblet cells and undergo a >1,000-fold expansion upon secretion, a process requiring sufficient amounts of bicarbonate to raise the pH and chelate calcium ions (1). Insufficient amounts of bicarbonate causes the mucus to remain attached to the epithelium in the small intestine as a required enzyme cannot reach its target cleavage site in the mucin (2).

Cystic fibrosis (CF) is caused by a non-functional CFTR chloride and bicarbonate ion channel. However, the coupling between this and the main phenotype with mucus retention and accumulation has remained elusive until recently when we observed that the low amounts of bicarbonate caused by the non-functional CFTR ion channel gave a poor expansion of newly secreted mucin (1). No treatments directly addressing the mucus/mucin abnormality in CF are available, although several treatments like hypertonic saline and mannitol probably affect mucus retention. Most novel therapies for CF are addressing the dysfunctional CFTR channel. These therapies are all dependent on the specific mutation causing disease and are thus individual. No therapies addressing the abnormal mucus for all CF patients are available.

Bronchitis, chronic bronchitis, COPD and asthma are all characterized by mucus retention and accumulation. No major and efficient therapies addressing the stagnant mucus in these diseases are currently available.

Hence, there is a large demand in the art of improved methods and compositions of preventing and treating disorders in relation to dysfunction of the mucus system in the respiratory tract.

SUMMARY OF THE INVENTION

An object of the present invention is to at least partly overcome the above-mentioned drawbacks by providing uses, methods and compositions which allow for efficient prevention and/or treatment of disorders related to dysfunctions in the respiratory tract.

These objects are achieved, in a first aspect, by means of a compound capable of binding calcium ions, said compound comprising gamma-carboxy glutamic acid (Gla) and/or derivatives thereof, which compound is defined according to Formula 3:

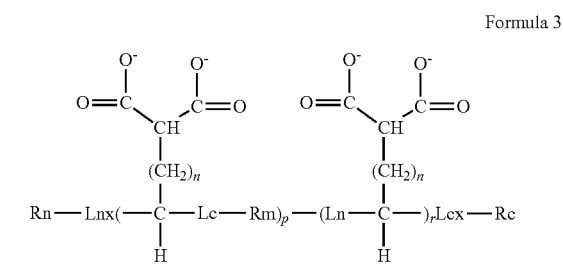

Formula 3 wherein n is 0 or an integer 1-10, such as 0, 1, 2, 3, 4, 5, 6, 7, 8, 9, or 10, such as from 1 to 5, such as 1;

p is an integer 1-20; such as 1, 2, 3, 4, 5, 6, 7, 8, 9, 10, 11, 12, 13, 14, 15, 16, 17, 19, or 20; for example 2-11, such as 4-11;

r is an integer 1-20, such as 1, 2, 3, 4, 5, 6, 7, 8, 9, 10, 11, 12, 13, 14, 15, 16, 17, 19, or 20;

under proviso that p+r equals 3, 4, 5, 6, 7, 8, 9, 10, 11, 12, 13, 14, 15, 16, 17, 19, or 20, and typically p+r equals 5, 6, 7, 8, 9, 10, 11 or 12;

wherein each of Rn, Rm, Rc, Lc, Ln, Lcx, and Lnx is independently present or absent, and where present, Ln is independently selected from: —NH—; and any one of formula (A)-(F):

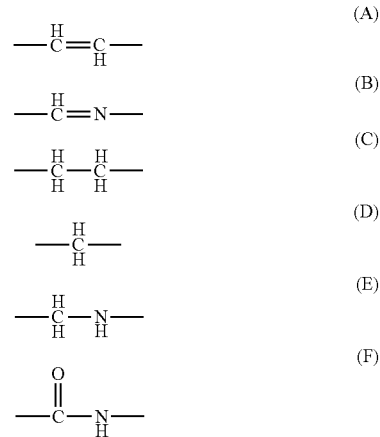

Lc is independently selected from: —CO—; and any one of formula (A)-(F) above;

or, provided Rm is absent, Ln and Lc together forms a linker according to any one of formula (A)-(F);

Lnx is —NH—;

Lcx is —CO—;

Rn is independently selected from: —$H_2^+$; —$CH_3$; 1-20 repetitions of any naturally occurring amino acid; Ser substituted with mono- or oligosaccharide; Thr substituted with mono- or oligosaccharide; and a hydrocarbon chain with up to five carbon atoms.

Rm is independently selected from —$CH_2$—; 1-20 repetitions of any amino acid; Ser substituted with mono- or oligosaccharide; Thr substituted with mono- or oligosaccharide; and a hydrocarbon chain having up to 5 carbon atoms; and Rc is independently selected from —$O^-$; —$CH_3$; 1-20 repetitions of any naturally occurring amino acid; Ser substituted with mono- or oligosaccharide; Thr substituted with mono- or oligosaccharide; and a hydrocarbon chain with up to five carbons.

The present inventors have found that compounds based on gamma-carboxy glutamic acid peptides and related compounds as defined herein can be effective in treating and/or preventing the mucus accumulation and stagnation that characterizes many respiratory diseases and disorders.

The claimed compounds have been found to bind calcium with high affinity, and generally, longer peptides to bind with higher affinity than shorter peptides. For instance, a Gla-peptide according to embodiments of the invention having four units (GlaX4) was effective at detaching the mucus from CF mouse ileum. Furthermore, a compound according to embodiments of the invention comprising 8 units of gamma-carboxy glutamic acid is capable of binding calcium in low nanomolar concentrations. In fact, while the N-terminal part of mucins binds calcium in low nanomolar concentrations at the pH found in cellular storage granulae, a compound according to embodiments of the present invention having 8 gamma-carboxy glutamic acid residues (GlaX8) was able to compete out calcium from the mucin at low nanomolar concentration.

Together, the results of the extensive experimentation underlying the present invention provide far-reaching evidence for the usefulness of pharmaceutical compounds based on gamma-carboxy glutamic acid and related calcium binding compounds in the treatment of diseases related to stagnated mucus in upper and/or lower respiratory tracts.

A particular advantage of using compounds based on gamma-carboxy glutamic acid peptides as defined herein is that gamma-carboxy glutamic acid as such is a naturally occurring amino acid, existing in for example the blood and bone. Since this amino acid is naturally occurring less negative side effects may be expected when used as a medicament as compared to other possible treatments. Furthermore, compounds according to embodiments of the invention are advantageous with respect to degradation properties, as they are typically not degraded in the respiratory tract, but well if swallowed into the gastrointestinal tract.

In embodiments of the invention, Rm is independently selected from —$CH_2$—; Ser substituted with mono- or oligosaccharide; Thr substituted with mono- or oligosaccharide; and a hydrocarbon chain having up to 5 carbon atoms.

In embodiments of the invention, Rn may be —$H_2^+$ and/or Rc may be —O. Furthermore, in embodiments of the invention, at least one Rm may be absent. In some embodiments, all Rm may be absent.

In embodiments of the invention, n may be from 0 to 10, such as 0, 1, 2, 3, 4, 5, 6, 7, 8, 9 or 10. For instance, n may be from 1 to 5, from 1 to 3, or typically 1.

In embodiments of the invention the number of Gla units may be from 2 to 20, such as from 3 to 12, for example from 5 to 10, such as from 6 to 8. In Formula 3 above this represents p being an integer of from 1 to 19, such as an integer from 2 to 11, such as an integer from 4 to 9, such as an integer from 5 to 7, such as 7. For example, the present inventors have demonstrated the effects of compounds according to formula Formula 3 in which Rn is —$H_2^+$, Rm is absent, Rc is —$O^-$, n is 1 and p is selected from the group consisting 1, 3, 5, 7, 9 and 11. In particular, Rn may be —$H_2^+$, all Rm may be absent, Rc may be —$O^-$, n may be 1 and p may be 7.

As used herein, "all $R_m$ are absent" means that each gamma-carboxy glutamate unit of said compounds is directly coupled to the next gamma-carboxy glutamate unit, via a peptide bond or another linker (A)-(E) as defined below. The expression "at least one Rm is absent" means that at least two gamma-carboxy glutamate units are coupled directly to one another via a peptide bond or another linker (A)-(E).

In another aspect, the present invention relates to a compound capable of binding calcium ions comprising at least two gamma-carboxy glutamate units each defined according to Formula 1

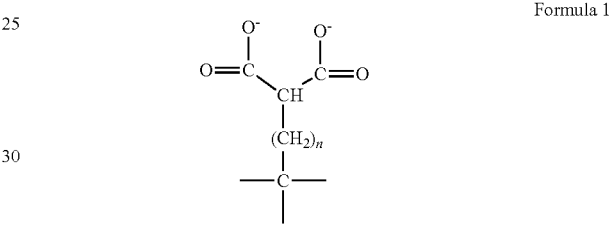

Formula 1 wherein n is 0, 1, 2, 3, 4, 5, 6, 7, 8, 9 or 10;
said compound comprising a linker between at least two gamma-carboxy glutamate units, which linker is selected from any one of formula A-E:

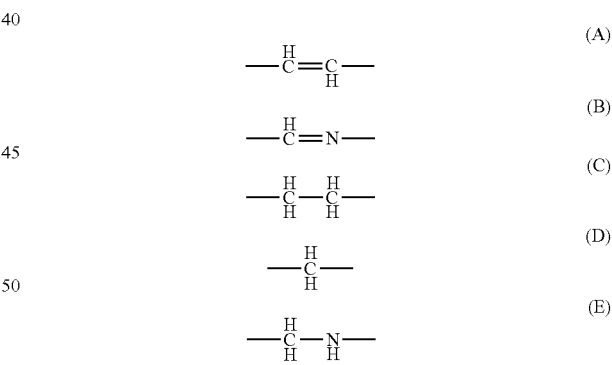

In another aspect, the present invention relates to the use of a compound as defined above according to Formula 3 or Formula 1 for use as a medicament, in particular for use in the treatment and/or prevention of a disorder characterized by mucus stagnation in the upper and/or lower respiratory tract. The invention also relates to the use of a calcium binding compound as defined herein in the manufacture of a medicament, in particular for the treatment of a disorder characterized by mucus stagnation in the upper and/or lower respiratory tract.

The major constituent in mucus is the mucins. These are packed in vesicles of the producing cells due to low pH (5.5-6) and calcium. Upon release, the mucin has to be unpacked and expanded >1,000-fold, something that require the removal of calcium ions. If this process is insufficient, as in cystic fibrosis, the mucin and mucus is attached to the epithelium and cannot be moved or transported. Gamma-carboxy glutamic acid is a natural amino acid of the body and is able to chelate calcium ions. Gamma-carboxy glutamic acid has been shown to exist in nature clustered as two units, and although it could in theory, according to known gene sequences, appear clustered with up to maximum four units, such peptides have not actually been shown to exist in nature.

Examples of diseases and/or disorders which are related to mucus accumulation and stagnation in the respiratory tract and which may be treated by compounds based on gamma-carboxy glutamic acid peptides in accordance with embodiments of the present invention include:

Upper respiratory diseases, such as rhinitis, chronic rhinitis, cystic fibrosis, sinusitis.

Lower respiratory diseases, such as acute bronchitis, chronic bronchitis, chronic obstructive pulmonary disease (COPD), emphysema, asthma, cystic fibrosis, bronchiectasis.

Disorders of the respiratory tract with accumulation of mucus.

In yet another aspect, the present invention relates to a compound capable of binding calcium ions, said compound comprising at least two gamma-carboxy glutamate units, wherein each gamma-carboxy glutamate unit is defined by Formula 1:

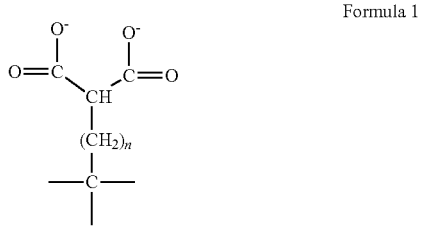

Formula 1 wherein n is 0, 1, 2, 3, 4, 5, 6, 7, 8, 9 or 10,
for use in the treatment and/or prevention of a disorder characterized by mucus stagnation in the upper and/or lower respiratory tract. The compound may comprise a linker between at least two gamma-carboxy glutamate units, which linker is selected from Formula A, B, C, D, E and F:

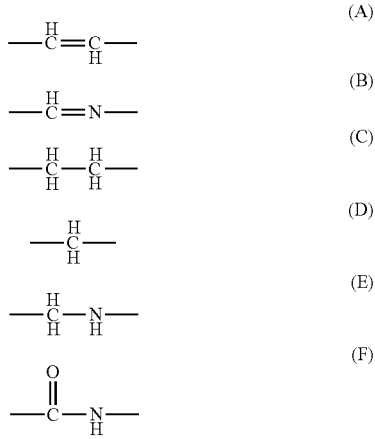

Typically, the gamma-carboxy glutamate units are separated only by said linker.

In embodiments, the linker may be a peptide bond (F).

In embodiments, the compound may comprise at least 3 gamma-carboxy glutamate units according to formula 1, wherein adjacent units are separated only by a linker.

Optionally, the compound may comprise at least 3, at least 4, at least 5, at least 6, at least 7 or at least 8 gamma-carboxy glutamate units.

The present inventors have found that a compound comprising gamma-carboxy glutamate units may advantageously have a number of gamma-carboxy glutamate units from 4 to 12, from 6 to 12 or from 6 to 10. A compound having 8 gamma-carboxy glutamate units has been shown to be particularly effective. It should be noted that this applies to the compounds comprising gamma-carboxy glutamate according to any one of the different definitions given herein.

In another aspect, the invention provides a compound as defined above by formula 3 for use as a medicament, in particular in the treatment and/or prevention of a disorder characterized by mucus stagnation in the upper and/or lower respiratory tract.

In a yet another aspect, the present invention relates to a pharmaceutical composition comprising a therapeutically effective amount of a compound capable of binding calcium ions as defined herein, and a pharmaceutically acceptable carrier and/or excipient.

Furthermore, in addition to the usefulness of the gamma-carboxy glutamate compounds and derivatives described herein as such, the present inventors found that carbonate ions provided by the addition of sodium bicarbonate could potentiate the terapeutic effect of these said compounds when used for treatment of mucus stagnation and accumulation. Hence, in embodiments of the invention, the pharmaceutical composition may advantageously further comprise a source of carbonate ions, for instance sodium bicarbonate.

In a further aspect, the invention relates to a method of treatment and/or prevention of a disorder characterized by mucus stagnation in the upper and/or lower respiratory tract, comprising administering to a patient in need thereof a therapeutically effective amount of a compound capable of binding calcium ions comprising at least two gamma-carboxy glutamate units as defined herein.

It is noted that the compositions, uses and methods according to embodiments of the present invention may involve a combination or mixture of compounds having different number of gamma-carboxy glutamate units. For instance, a pharmaceutical composition according to embodiments of the invention may comprise a compound according to any definition given herein, having a first number of Gla units, such as 8, and additionally a compound according to any definition given herein, having a second, different number of Gla units, such as 6, and optionally a further compound as defined herein, having yet another, different number of Gla units. Hence, a pharmaceutical composition may comprise several (at least two) different Gla peptides. Similarly, a method of treatment and/or prevention as described herein, or the use of a compound for treatment as described herein, may optionally involve a combination of compounds having different numbers of Gla units.

BRIEF DESCRIPTION OF THE DRAWINGS

These and other aspects of the present invention will now be described in more detail, with reference to the appended drawings.

DETAILED DESCRIPTION OF THE INVENTION

Figure 1A:
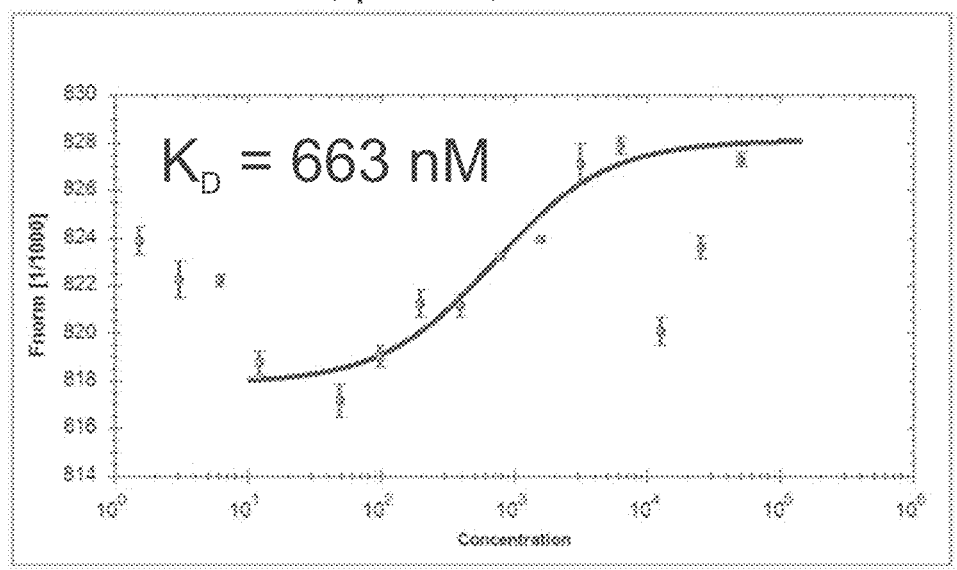
FIGS. 1A and 1B are graphs showing binding of calcium ions to Gla-peptide with six units (GlaX6) at pH 5.5 and 7.3.

The invention will now be further explained in the following embodiments and experimental examples. These are only intended to illustrate the invention and should in no way be considered to limit the scope of the invention.

The present inventors have found that compounds based on gamma-carboxy glutamic acid peptides as defined herein can be effective in treating and/or preventing the mucus accumulation and stagnation that characterizes many respiratory diseases and disorders. This insight was preceded by extensive experimentation, which is presented further below.

According to embodiments of the invention, the compound is capable of binding calcium ions, and comprises at least two gamma-carboxy glutamate units, wherein each gamma-carboxy glutamate unit is defined by Formula 1:

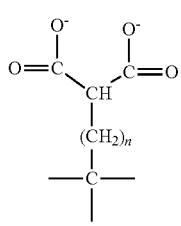

Formula 1 wherein
n is 0, 1, 2, 3, 4, 5, 6, 7, 8, 9 or 10. For example, n may be from 1 to 5, such as from 1 to 3. Typically, n may be 1.

Such compounds have been found to be useful in the treatment and/or prevention of a disorder characterized by mucus stagnation in the upper and/or lower respiratory tract.

A compound according to other embodiments of the invention is capable of binding calcium ion and comprises gamma-carboxy glutamic acid (Gla) and/or derivatives thereof, and may be defined according to Formula 3:

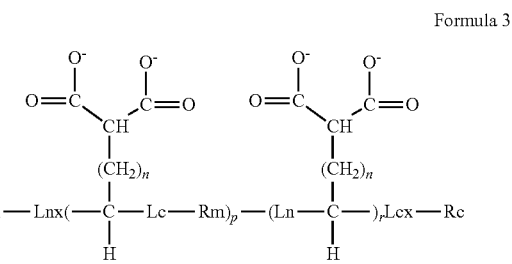

Formula 3 wherein
n is 0 or an integer 1-10, such as 0, 1, 2, 3, 4, 5, 6, 7, 8, 9, or 10, such as from 1 to 5, such as 1;

p is an integer 1-20; such as 1, 2, 3, 4, 5, 6, 7, 8, 9, 10, 11, 12, 13, 14, 15, 16, 17, 19, or 20; for example 2-11, such as 4-11;

r is an integer 1-20, such as 1, 2, 3, 4, 5, 6, 7, 8, 9, 10, 11, 12, 13, 14, 15, 16, 17, 19, or 20;

under proviso that p+r equals 3, 4, 5, 6, 7, 8, 9, 10, 11, 12, 13, 14, 15, 16, 17, 19, or 20, and typically p+r equals 5, 6, 7, 8, 9, 10, 11 or 12;

wherein each of Rn, Rm, Rc, Lc, Ln, Lcx, and Lnx is independently present or absent, and where present, Ln is independently selected from: —NH—; and any one of formula (A)-(F):

 (A)

 (B)

 (C)

 (D)

 (E)

 (F)

Lc is independently selected from: —CO—; and any one of formula (A)-(F) above;

or, provided Rm is absent, Ln and Lc together forms a linker according to any one of formula (A)-(F);

Lnx is —NH—;

Lcx is —CO—;

Rn is independently selected from: —H$_2^+$; —CH$_3$; 1-20 repetitions of any naturally occurring amino acid; Ser substituted with mono- or oligosaccharide; Thr substituted with mono- or oligosaccharide; and a hydrocarbon chain with up to five carbon atoms.

Rm is independently selected from —CH$_2$—; 1-20 repetitions of any amino acid; Ser substituted with mono- or oligosaccharide; Thr substituted with mono- or oligosaccharide; and a hydrocarbon chain having up to 5 carbon atoms; and Rc is independently selected from —O$^-$; —CH$_3$; 1-20 repetitions of any naturally occurring amino acid; Ser substituted with mono- or oligosaccharide; Thr substituted with mono- or oligosaccharide; and a hydrocarbon chain with up to five carbons.

Alternatively, the compounds for use in the present invention, for example in a pharmaceutical composition and/or a treatment of a disorder characterized by mucus stagnation in the upper and/or lower respiratory tract may comprise at least two gamma-carboxy glutamate units each defined according to Formula 1 above. A compound comprising at least two gamma-carboxy glutamate units each defined according to Formula 1 may optionally comprise a linker between at least two gamma-carboxy glutamate units. The linker may be selected from any one of formula A-E:

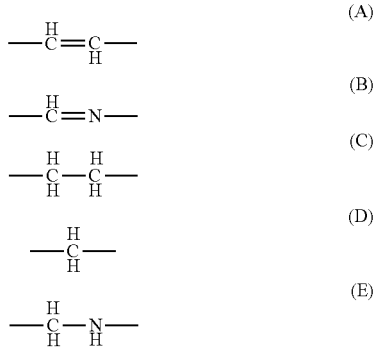

In embodiments of the invention, a linker between at least two gamma-carboxy glutamate units may be a peptide bond.

As used herein, the expression "gamma-carboxy glutamate unit" refers to a single gamma-carboxy glutamic acid residue, and is intended to also encompass derivatives, such as units having more than one sidechain CH$_2$ moiety (n≥2).

As used herein, the expressions "calcium binding" or "capable of calcium binding", and "capable of binding calcium ions" are intended to mean that a compound is capable of binding Ca$^{2+}$.

A compound according to embodiments of the invention may advantageously be capable of binding to Ca$^{2+}$ such that the K$_D$ value of the interaction is at least 1×10$^{-8}$ M at pH 7.3. However, the calcium ion binding capacity of the compound or composition according to embodiments of the invention should be balanced, as too high afficinty for calcium is potentially severely toxic as it can withdraw calcium from living cells.

As used herein, "mucus stagnation" means accumulation of mucus, especially in the respiratory tract, due to overproduction of mucus and/or deficient mucus transport away from the site of production.

A pharmaceutical composition, useful in treatment of mucus accumulation or mucus stagnation in the respiratory tract, may comprise a therapeutically effective amount of a compound capable of binding calcium ions as defined herein, and a pharmaceutically acceptable carrier and/or excipient. The pharmaceutical composition may for instance additionally comprise any one of a salt, a pH regulator, an oil, a preservative, an osmotically active agent, and any combination thereof.

The compounds and compositions described herein may advantageously be used in a method of treatment and/or prevention of a disorder characterized by mucus stagnation in the upper and/or lower respiratory tract. Such methods may typically comprise administering, to a patient in need thereof, a therapeutically effective amount of a compound capable of binding calcium ions comprising gamma-carboxy glutamate units as defined herein.

As shown in the examples and Figures, the present inventors have found that compounds comprising gamma-carboxy glutamate units as defined herein are capable of inducing mucus detachment of at least part of a mucosal surface affected by a lack of or deficiency of functioning CFTR ion channels, in other words a mucosal surface displaying CFTR dysfunction (e.g. a mucosal surface in a CF patient). In particular, the compounds are able to cause or induce at least partial detachment of mucus from the epithelium of the mucosal surface and thereby return the abnormal mucus of that surface (e.g. the abnormal mucus of a CF patient) to a normal phenotype (i.e. the phenotype of a mucosal surface that is not displaying CFTR dysfunction e.g. a non-CF phenotype). This effect may in particular be achieved when the compounds comprising gamma-carboxy glutamate units as defined herein are administered in an amount sufficient to achieve a local concentration of the compounds of from 100 nM to 1 mM at the apical side of the epithelium, i.e. the lumen/mucus interface. However, it is conceivable that also lower and/or higher local concentrations may achieve a desirable therapeutic effect. Hence, a therapeutically effective amount as mentioned above may be an amount sufficient to achieve a local concentration of from 1 nM to 10 mM upon administration.

The present inventors have found that in order to achieve detachment of mucus from the epithelial cells of a mucosal surface affected by a lack of functional CFTR (i.e. a mucosal surface displaying CFTR dysfunction), certain local concentrations of the compounds defined herein are useful at the mucosal surface. This means that compound(s) as defined herein may be administered or delivered, such that the compounds present at, or reaching, the mucosal surface are present at this concentration, and more specifically that the concentration of said compounds at the mucus layer, or at the mucus coating, may be within this range. Thus, for example, the local concentration at the lumen of at least part of a mucosal surface or at the mucus interface of at least part of a mucosal surface may be within this range. In particular this concentration is achieved at the apical side of the epithelium, or mucosal surface.

In certain embodiments the local concentration of the compound(s) comprising gamma-carboxy glutamate units as defined herein may be from 1 nM to 10 mM, for instance from 10 nM to 10 mM, from 20 nM to 10 mM or from 100 nM to 10 mM, such as from 100 nM to 5 mM. In other embodiments the local concentration of the compound(s) comprising gamma-carboxy glutamate units as defined herein may be from 1 nM to 5 mM, such as from 1 nM to 1 mM, or from 10 nM to 5 mM, or from 100 nM to 5 mM.

In other embodiments the local concentration of the compound(s) comprising gamma-carboxy glutamate units as defined herein may be 1 nM to 1 μM, such as 1 nM to 500 μM, 1 nM to 200 μM or 1 nM to 100 μM. In other embodiments the local concentration of the compound(s) comprising gamma-carboxy glutamate units as defined herein may be 100 nM to 1 mM, 100 nM to 500 μM, or 100 nM to 100 µM., or 100 nM to 10 µM. In other embodiments the local concentration of the compound(s) comprising gamma-carboxy glutamate units as defined herein may be from 500 nM to 1 µM or less, for example 500 nM to 900 µM, 500 nM to 500 µM, or 500 nM to to 100 µM.

In other embodiments the local concentration of the compound(s) comprising gamma-carboxy glutamate units as defined herein may be up to from 1 µM to 10 mM, 1 µM to 5 mM, such as 1 µm to 1 mM or less, e.g. from 1 µm to 900 µM, 1 µM to 500 µM, 1 µM to 200 µM or 1 µM to 100 µM.

In other embodiments the local concentration of the compound(s) comprising gamma-carboxy glutamate units as defined herein may be equal to or above 1 nM and less than 1 µM, e.g. 1 to 900 nM, 1 to 500 nM, or 1 to 100 nM, for 10 to 900 nM, 10 to 500 nM, or 10 to 100 nM.

The route of administration may in particular be nasal and/or tracheal-bronchial.

The work described in the appended drawings and experimental examples shows that compound(s) comprising gamma-carboxy glutamate units as defined herein are capable of promoting the conversion of the abnormal phenotype of a mucosal surface affected by a lack of functional CFTR ion channels, and more specifically a mucosal surface from a CF patient, to a phenotype more closely resembling that of a healthy mucosal surface, i.e. a mucosal surface from a subject that is not affected by a lack of functional CFTR ion channels (e.g. a non-CF subject). This is in part believed to be due to the observed detachment of the mucus layer from the mucosal surface affected by a lack of functional CFTR ion channels (e.g. a CF mucosal surface) upon exposure of the mucosal surface to said compound(s) comprising gamma-carboxy glutamate units as defined herein at certain local concentrations. A mucus layer from a mucosal surface affected by a lack of functional CFTR ion channels that has been detached in accordance with the treatments of the invention is proposed to behave substantially analogously to a normal healthy mucus layer that is not affected by a lack of functional CFTR ion channels and therefore respond to the body's mucus clearance/handling systems in much the same way as the mucus of a healthy subject (e.g. a non-CF subject).

This is expected to result in the alleviation of the condition suffered by the patient undergoing treatment, and/or of any complication or disorder etc. associated with the condition, and/or the prevention of the onset of any further condition or disorder or complication associated with the condition. In the particular case of CF this is expected to result in alleviation of the CF-associated disorders or conditions (complications of CF) suffered by the CF patient undergoing treatment and/or prevention of the onset of further CF-associated disorders or conditions (complications of CF), e.g. those discussed above.

In view of this, full (or complete) detachment within the treatment area might not be necessary to give noticeable improvement in a patient's (e.g. a CF patient's) conditions or disorders. As such, in certain embodiments the detachment may be partial. Partial detachment in accordance with the invention can be considered to be that extent of detachment that is therapeutically effective. Any improvement in any of the symptoms or indicators of a condition (for example CF), e.g. the various CF-associated disorders or conditions (complications of CF) displayed by a CF patient, or any complication or symptom or condition associated with any other CFTR dysfunction-related condition in the patient undergoing treatment, or any prophylactic or preventive effect in the patient, can be considered indicative that therapeutically effective detachment has been achieved.

Expressed numerically the mucus layer at the target treatment area may be detached over at least 40% of that area, e.g. at least 50, 60, 70, 75, 80, 85, 90, 95, 96, 97, 98, or 99% of that area. Preferably the mucus layer detachment corresponds to 100% of the target treatment area. Detachment may also be viewed as a reduction in mucus adhesiveness or a loosening in the interaction between the mucus layer and the underlying epithelial cells. Partial detachment can therefore be considered to be a reduction in mucus adhesiveness/loosening in mucus-epithelium interaction of at least 40%, e.g. at least 50, 60, 70, 75, 80, 85, 90, 95, 96, 97, 98, 99% or about 100%.

The extent of detachment can be measured by any conventional means, e.g. microscopically. The extent of detachment can further be correlated to reduction in mucus adhesiveness/loosening in mucus-epithelium interaction. As shown in the experimental examples, a portion of the mucosal surface of the treatment area can be extracted, e.g. by biopsy during endoscopy, and the extent of the detachment of the mucus layer can be measured by measuring mucus thickness before and after a standardized aspiration procedure. Repeating this procedure at a plurality of different locations allows the assessment of the degree of detachment over a certain area. In these, and equivalent, embodiments mucus detachment can also be expressed in terms of average (e.g. mean) mucus thickness over the treatment area following aspiration. Preferably partial detachment may result in a reduction of the average (e.g. mean) mucus thickness over the treatment area of at least 40%, e.g. at least 50, 60, 70, 75, 80, 85, 90, 95, 96, 97, 98, 99% or about 100% following aspiration. Depending on the technique used to aspirate the mucus layer it might not be possible to completely remove the mucus layer even though detachment is total (such as would be the case in a sample from a healthy subject or more specifically a mucosal surface which is not affected by a lack of functional CFTR, e.g. a non-CF sample). In such instances 100% should be construed as the maximum thickness reduction that is observed in the experimental context. Maximum thickness reduction can be determined by suitable internal experimental controls.

Mucus attachment can also be recorded and observed by video microscopy where mucus should be normally moved by cilia. The mucus can be visualized by different staining including charcoal and dyes.

It is envisaged that the treatment may involve simultaneous and/or concomitant co-administration of another therapeutically active agent useful for treatment of the same disorder(s), such as hypertonic saline or osmotically active agents, or pH adjusting agents. Furthermore, sodium bicarbonate may be co-administered with a compound according to embodiments of the invention.

It is expected that the therapeutic effect of the compounds and compositions described herein may be immediate and/or transient. It is therefore envisaged that a method of treatment using a compound according to embodiments of the invention may involve administration from once per day up to 20 times per day, for instance from 3 times per day to 10 times per day.

By the term "pharmaceutically effective amount" is herein meant an amount of a compound as defined herein which is effective to reduce the amount of mucus retained and accumulated in the nasal and/or respiratory tract.

The term "patient" as used herein encompasses human or animals in need of treatment and/or prevention of a disorder characterized by mucus stagnation in the upper and/or lower respiratory tract.

Disorders characterized by mucus stagnation in the upper respiratory tract and/or the lower respiratory tract include respiratory and/or nasal diseases, such as acute rhinitis; chronic rhinitis; sinuitis; acute bronchitis; chronic bronchitis; chronic obstructive pulmonary disease (COPD); emphysema; bronchiectasis; respiratory inflammatory or allergic disease, such as a systemic inflammatory disease associated with respiratory mucus stagnation and mucus overproduction; asthma; cystic fibrosis; and bacterial infection. The compounds and compositions according to embodiments of the invention may be particularly useful in the treatment and/or prevention of cystic fibrosis.

As used herein, "local concentration" means the concentration of the administered compound(s) comprising gamma-carboxy glutamate units as defined herein present at the mucosal surface, or more particularly at the mucus layer or coating, e.g. at the lumen/mucus interface, of the target treatment area (which may be at least part of the target mucosal surface). Accordingly, "at the mucosal surface", "at the mucus layer or coating of the mucosal surface" or "at the lumen/mucus interface of the mucosal surface" (which terms are used interchangeably) can be expressed as the "immediate vicinity" of the apical surface of the mucus layer or as "essentially in direct contact" with the apical surface of the mucus layer. Expressed numerically a spatial point less than 1 mm from the apical surface of the mucus layer, e.g. less than 0.5, 0.25, 0.1, 0.05, 0.01, 0.005, 0.001 mm from the apical surface of the mucus layer is at the lumen/mucus interface. In other embodiments the term "local concentration" includes that present within the mucus layer of the mucosal surface at the target treatment area. Typically, in patients in need of treatment, the target mucus layer will essentially be fully attached, or partially attached, to the underlying epithelium. The volume under consideration will ultimately be limited by the thickness of the mucus at the target area, which may vary depending on the location of the treatment area, the patient and the severity of their clinical condition, e.g. their CF. In certain embodiments the local concentration is that concentration within the mucus at the lumen/mucus interface. Expressed numerically a spatial point at a depth of less than 1 mm below the apical surface of the mucus layer, e.g. less than 0.5, 0.25, 0.1, 0.05, 0.01, 0.005, 0.001 mm below the apical surface of the mucus layer is at the lumen/mucus interface. In further embodiments local concentration will determined as the concentration (or mean average concentration) present throughout the full depth of the mucus layer at the target treatment area.

In the context of the present invention the "local concentration" will typically correspond to the concentration of the compound(s) comprising gamma-carboxy glutamate units found in the body fluid present at the lumen/mucus interface of the target mucosal surface, (e.g. in the respiratory tract and paranasal sinuses). However as mentioned above the term "local concentration" also includes any concentration of compound(s) comprising gamma-carboxy glutamate units present within the mucus layer of the mucosal surface at the target treatment area.

The relevant volume of the solvent/mucus will be determined in part by the size of the target treatment area under consideration. This may be all or part of the respiratory tract, the paranasal sinuses, e.g. those parts recited below, or a subsection thereof. As mentioned above "at the lumen/mucus interface" of the mucosal surface of the target treatment area means a spatial point less than 1 mm from the apical surface of the mucus layer.

The person skilled in the art will be able to determine routinely the amount of a compound comprising gamma-carboxy glutamic acid units according to embodiments of the invention to administer in order to achieve the desired concentration thereof at the lumen/mucus interface of the mucosal surface at the target treatment area. This amount will vary depending on the location of the target treatment area, the route of administration and dosage form being used. Any improvement in any of the symptoms or indicators of the condition being treated in accordance with the invention in a patient (for example CF or any of the other above-mentioned conditions), or e.g. in the various CFTR dysfunction-associated (e.g. CF-associated) disorders or conditions (complications) of CF, or any other condition, displayed by the patient, or any prophylactic or preventative effect in such a patient, can be considered indicative that the appropriate local concentration has been achieved.

The local concentration can be measured directly to ensure appropriate dosing. This may be achieved through sample extraction and analysis or by imaging labelled versions of the compound(s) according to embodiments of the invention. Suitable sample collection techniques will depend on the target treatment area, but in general can include sputum collection (respiratory tract), swabbing (e.g. nose, mouth and throat), mucus biopsy and tissue biopsy, e.g. via an endoscopic procedure. Such procedures include rhinoscopy (nose/sinus), bronchoscopy (lower respiratory tract), Labelled compound(s) according to embodiments of the invention may be radioactive or luminescent (e.g. fluorescent). The signals emanating from such labelled compound(s) can be detected via appropriate means and quantified and then used to calculate local concentration.

The mucosal surface may be in the respiratory system, e.g. the upper respiratory tract (nose, nasal passages, pharynx larynx and trachea), the paranasal sinuses and the bronchi (primary, secondary and tertiary) and bronchioles of the lower respiratory tract. Preferably the mucosal surface will be in the respiratory tract, preferably the trachea, bronchi and bronchioles.

Inducing mucus detachment from the epithelial cells of the mucosal surfaces of the respiratory system affected by a lack of functional CFTR ion channels is proposed to result in improved mucociliary clearance and improvement in the condition being treated, in particular respiratory tract conditions associated with cystic fibrosis or with any of the other conditions/respiratory tract complications of cystic fibrosis or any of the disorders mentioned above.

Further embodiments of the invention are described in the itemized list of embodiments provided below. It is noted that the invention relates to all possible combinations of features recited in these items and/or in the claims.

EXAMPLES

Materials and Methods

Mice

Homozygous mice lacking a functional Cftr channel on C57BL/6 background (CF mice) were generated by heterozygous breeding, kept under specific pathogen free conditions in individually ventilated cages under controlled temperature (21-22° C.), humidity and 12 h light/dark cycle, maintained on special chow and water with PEG and salts to avoid distal ileal obstruction ad libitum and given regular water 4-7 days before the experiments. Ethical approval for the animal experiments was granted by the Ethics Committee for Animal experiments in Gothenburg.

Pigs

Homozygous Cftr knock out pigs (CF pigs) were generated by heterozygous breeding at Ludwig-Maximilians-Universitat in Munich, Germany.

Explant Tissue

Mice were euthanized by isoflurane and cervical dislocation. The distal ileum was removed and flushed with ice-cold 95% $O_2$/5% $CO_2$ Krebs solution (116 mM NaCl, 1.3 mM $CaCl_2$, 3.6 mM KCl, 1.4 mM $KH_2PO_4$, 23 mM $NaHCO_3$, and 1.2 mM $MgSO_4$), pH 7.4, and kept on ice during transportation (30 min). The tissue was opened along the mesenteric border, the longitudinal smooth muscle was removed, and the tissue was divided into two pieces and mounted in the horizontal Ussing-type perfusion chamber (4) with a circular opening of 4.9 $mm^2$. The chamber was mounted in a custom made heating block connected to a temperature controller (Harvard Apparatus, Holliston, Mass.), allowing the experiments to be performed at 37° C. The apical solution was kept unstirred to avoid disturbances to the mucus gel, whereas the serosal chamber was constantly perfused at a rate of 5 ml/h. Trans-epithelial potential difference (PD) was measured during the whole experiment using Calomel electrodes (Ref201; Radiometer, Copenhagen, Denmark) connected to the tissue bath via agar bridges (4% agar, 0.9% NaCl). The serosal chamber was constantly perfused with 95% $O_2$/5% $CO_2$ Krebs solution containing 10 mM glucose, 5.1 mM Na-glutamate, and 5.7 mM Na-pyruvate (Krebs-glucose). The apical chamber was filled with 150 µl likewise 95% $O_2$/5% $CO_2$-bubbled Krebs solution where glucose was substituted with 10 mM D-mannitol (Krebs-mannitol). After bubbling with 95% $O_2$/5% $CO_2$, the pH of these solutions was 7.4. Two adjacent parts of the tissue were analyzed in parallel.

Mucus Thickness Measurements

Figures 10A, 10B:
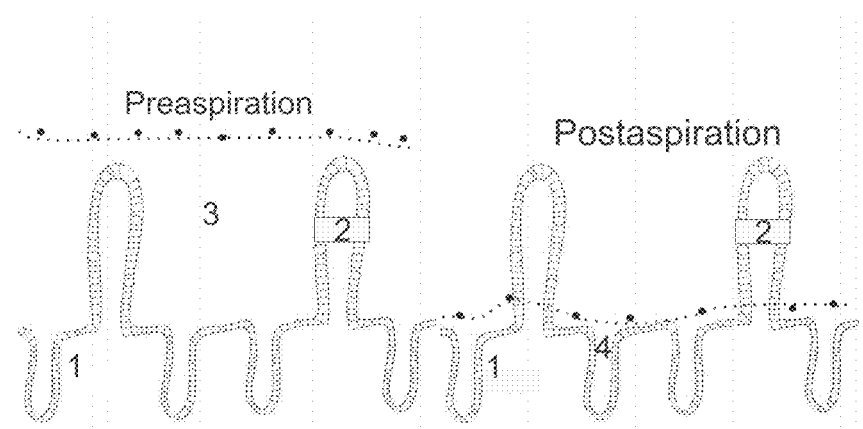
FIGS. 10A and 10B illustrate mucus thickness measurement in the ileum.

Mucus thickness was measured using a glass capillary connected to a micromanipulator and the mucus surface was visualized by allowing activated charcoal particles to sediment on top of the mucus (Fluka, Sigma-Aldrich, Stockholm, Sweden). Mucus thickness was assessed by measuring the distance between the charcoal particle and the villus tip (D) using a micropipette pulled to a tip diameter of 5-10 µm. The micropipette was mounted in a micromanipulator designed in house connected to a digimatic indicator (Mitotoyo, Tokyo, Japan). The tissue was viewed through a stereomicroscope at 40× magnification (Leica MZ125, Leica, Wetzlar, Germany). The level of the epithelial surface was determined as the point where the tip of the micropipette and the epithelial surface was in the same focal plane. The micropipette was kept at a constant angle of 40° and the vertical thickness of the mucus was obtained by multiplying the distance with cos 40. Five measurements were made for each time point, and the mean thickness was calculated and used as a single value. The adhesiveness of the mucus layer was assessed by comparing the total mucus thickness to the mucus thickness remaining after aspiration. The aspiration procedure was performed in a standardized way by using a small plastic Pasteur pipette (PP-101, outer tip diameter 0.9 mm, inner tip diameter 0.7 mm, max volume 800 µl; Cell Projects, Harrietsham, UK). The tip of the compressed pipette was placed on the edge of the chamber opening and the bulb of the pipette slowly opened over three seconds to aspirate the apical chamber solution and the non-adherent mucus. The size of the pipette allows for removal of the whole apical solution in one step. The remaining mucus thickness (denoted "Post") was measured after refilling the apical chamber with 150 µl Krebs-mannitol and the addition of new charcoal particles in order to avoid collapsing of any remaining mucus. After total removal of the mucus layer, the villus height was assessed by measuring the distance between the villi tips and the surface epithelium between the villi. Total mucus thickness is presented as the sum of these two measurements (FIG. 10).

Preparation of Apical Buffers

Buffers with 23 mM $NaHCO_3^-$ (original concentration) containing the different drug candidates were first bubbled with carbogen gas (5% $CO_2$, 95% $O_2$) and then the pH was adjusted to 7.4. In experiments where $NaHCO_3^-$ was increased to 46 mM (original concentration) the amount of NaCl was decreased correspondingly to maintain isomolarity. This buffer was also adjusted to pH 7.4. The buffers containing the drug candidates were all added to the apical (mucus surface) of the explants and the tissue incubated for 60 min on preformed mucus (mucus already formed when tissue was mounted). Mucus thickness was measured at 60 min and is illustrated by white bars and denoted "Pre" and after attempts to remove as "Post" aspiration.

Mounting and Alcian Blue Staining of Pig Trachea

Figure 11:
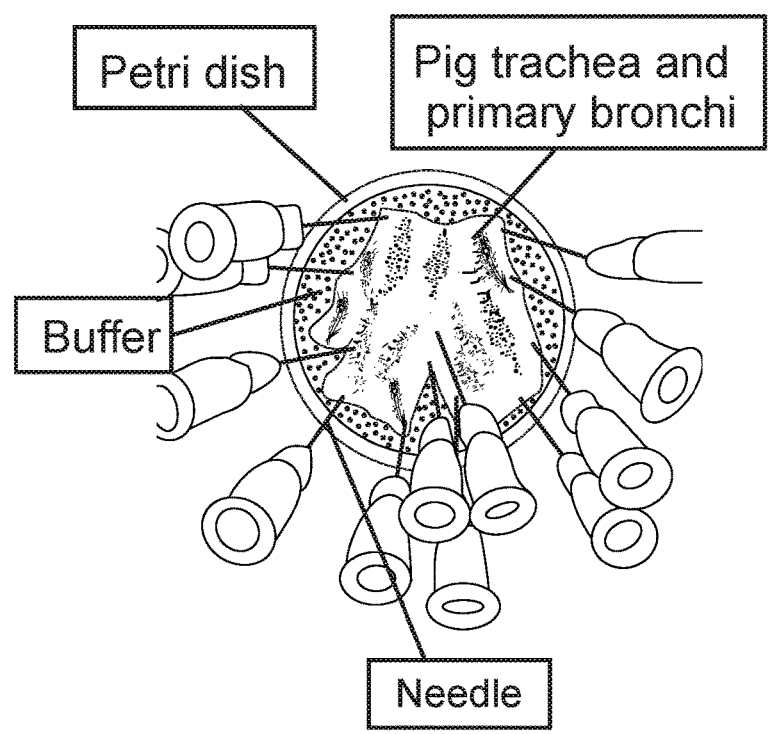
FIG. 11 illustrates a newborn piglet airway mounted in the experiment chamber.
Figure 12:
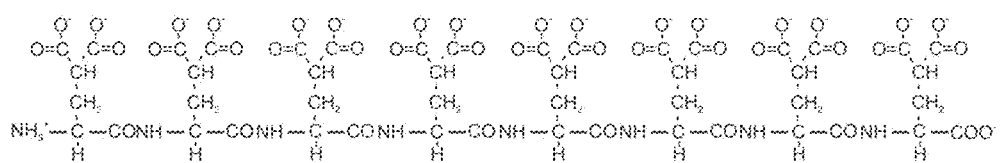
FIG. 12 shows the structural formula of an exemplary embodiment of the invention, represented by a peptide comprising 8 gamma-carboxy glutamate units directly linked to one another via peptide bonds.

The distal part of neonatal CF pig trachea together with the most proximal part of the primary bronchi were mounted in a Petri dish coated with Sylgard 184 Silicone Elastomer (Dow Corning, Wiesbaden, Germany) using G27 needles (FIG. 11). The tissue was covered in oxygenated (95% $O_2$, 5% $CO_2$) Krebs-glucose buffer and 0.4 Alcian blue 8GX (Sigma Aldrich, Stockholm, Sweden) pH 7.4 at room temperature. The Petri dish was placed in a custom made heating chamber which was gradually heated to 37° C. during a period of 10 min and kept at a constant temperature during the course of the experiment.

Video Microscopy

Tissue was monitored through a stereo microscope (Nikon, Tokyo, Japan) and time lapse recordings were acquired using a 5.0-megapixel color CCD camera (DS-Fi2, Nikon, Tokyo, Japan) and NIS elements software (Nikon, Tokyo, Japan). Alcian blue strand transport velocity was calculated using NIS elements. To calculate transport velocity, five measurements in each time lapse were performed on moving strands. The mean of these measurements were used to calculate mean transport velocity. The buffers containing the drug candidates were added to the tissue and incubated for 40 min before mucus transport was measured.

Labelling and Purification of GlaX6 and GlaX8 Peptides

Hexa (Glax6)- and Octa (Glax8)-diglutamic acid peptides were fluorescently labelled by incubation with a five-fold molar excess of fluorescin isothiocyanate, isomer I (FITC) for two hours at room temperature in the dark with gentle stirring (400 rpm). Free dye and FITC-labelled peptides were subsequently separated by size exclusion chromatography on a Superdex peptide column and eluted with 10 mM phosphate pH 7.4, 150 mM NaCl. Fractions containing the FITC-coupled Gla-peptides were further chromatographed on a Sephadex-G25 column in order to exchange the elution buffer.

Microscale Thermophoresis

Affinity experiments were carried out on a Monolith NT115.1 a Microscale Thermophoresis (MST) instrument equipped with a blue-green fluorescent reader. The interaction buffer for affinity analysis between MUC2N and calcium consisted of 50 mM 2-N-(morpholino)ethane sulfonic acid (MES) pH 5.5 and 150 mM NaCl for the analysis at acidic pH. $CaCl_2$ was titrated from a concentration of 500 µM to 15 nM and the MUC2N-GFP fusion protein added to give a final concentration of 460 nM MUC2N-GFP. Binding experiments at neutral pH were carried out in Tris-buffered saline (TBS) pH 7.4. For competition experiments the respective Gla-peptides were added at constant concentrations of 10 µM to the same dilution series of calcium as in the respective experiments.

In order to decipher the affinity between the Hexa- and the Octa-diglutamic acid peptides and calcium a dilution series of $CaCl_2$ ranging from 50 µM to 1.5 nM was prepared in MES for interaction analysis at pH 5.5 and in TBS at pH 7.4. Purified FITC-labelled Hexa- and Octapeptides were added at a constant concentration of app. 100 nM. MST traces were followed for 30 s after heat induction and the normalized ratio difference plotted against the different concentrations of calcium.

Additives

The effect of hypertonic saline, bicarbonate and osmotically active mannitol in the CF ileal explant model system have been studied and published (5, 6).

Results

Figure 1B:
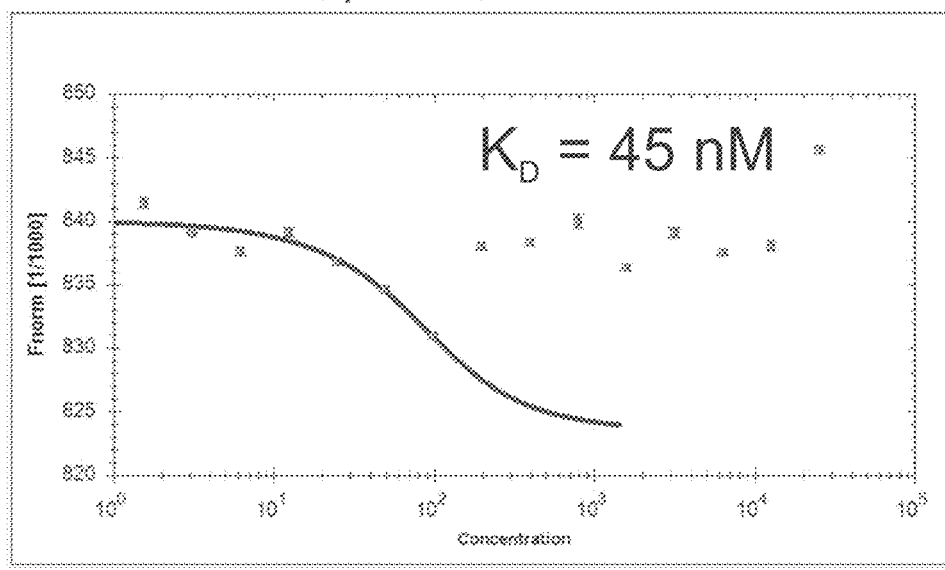

FIG. 1: Binding of calcium ions to Gla-peptide with six units (Glax6) at pH 5.5 and 7.3. FITC-labelled GlaX6 peptide were incubated with variable concentrations of calcium ions at pH 5.5 (A) and pH 7.3 (B). The thermophoretic mobility was measured revealing that calcium was binding to GlaX6 with 663 nM at pH 5.5 and 45 nM at pH 7.3. The curve at pH 7.3 is downwards showing that the molecule became smaller after calcium binding.

Figure 2A:
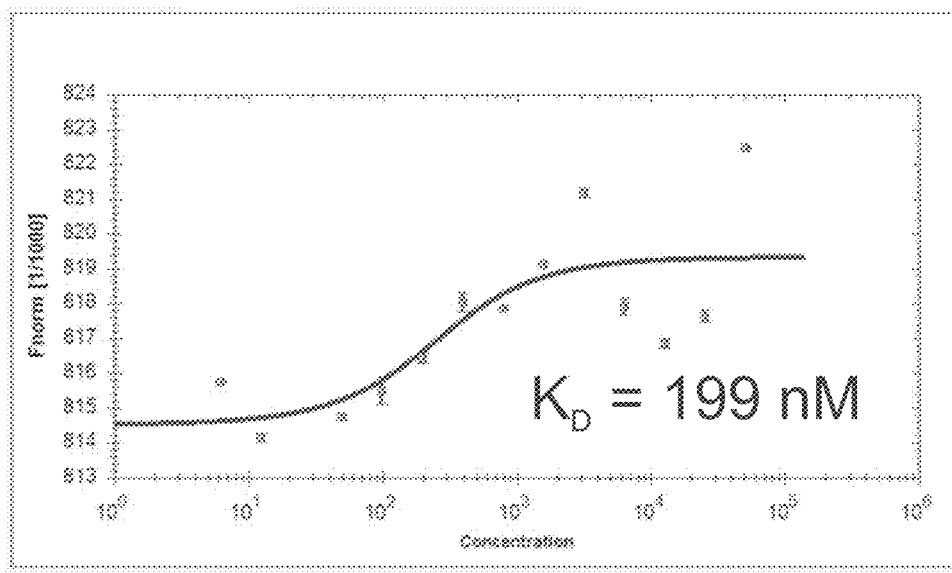
FIGS. 2A and 2B are graphs showing binding of calcium ions to Gla-peptide with eight units (Glax8) at pH 5.5 and 7.3.
Figure 2B:
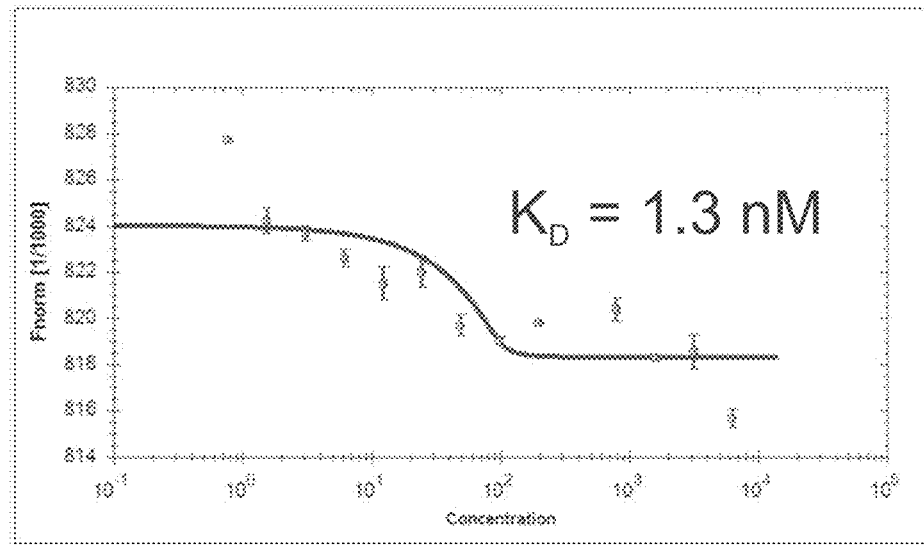

FIG. 2: Binding of calcium ions to Gla-peptide with eight units (Glax8) at pH 5.5 and 7.3. FITC-labelled GlaX8 peptide were incubated with variable concentrations of calcium ions at pH 5.5 (A) and pH 7.3 (B). The thermophoretic mobility was measured revealing that calcium was binding to GlaX8 with 199 nM at pH 5.5 and 1.3 nM at pH 7.3. The number of calcium ions bound to GlaX8 was about 8. The curve at pH 7.3 is downwards showing that the molecule became smaller after calcium binding.

Figure 3A:
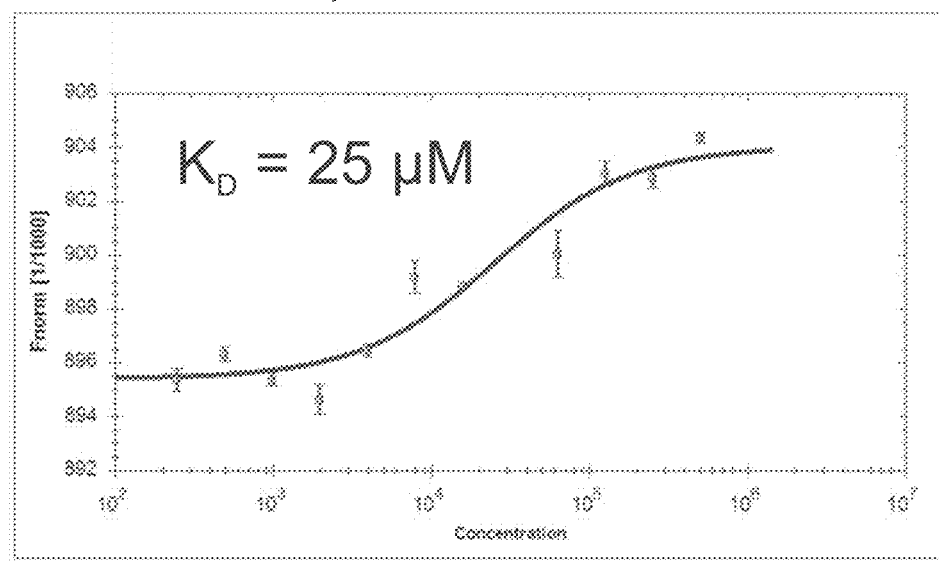
FIGS. 3A and 3B are graphs showing binding of calcium ions to the MUC2 mucin N-terminus at pH 5.5 and 7.3.
Figure 3B:
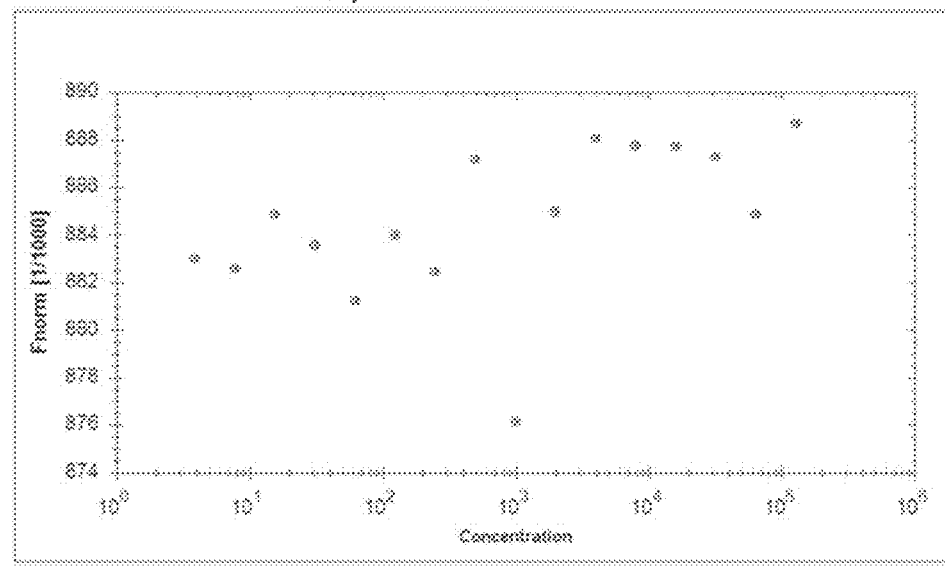

FIG. 3: Binding of calcium ions to the MUC2 mucin N-terminus at pH 5.5 and 7.3. GFP-labelled MUC2 mucin N-terminus were incubated with variable concentrations of calcium ions at pH 5.5 (A) and pH 7.3 (B). The thermophoretic mobility was measured revealing that calcium was binding to MUC2-N with an affinity of 25 µM at pH 5.5 and that no binding was observed at pH 7.3.

Figure 4A:
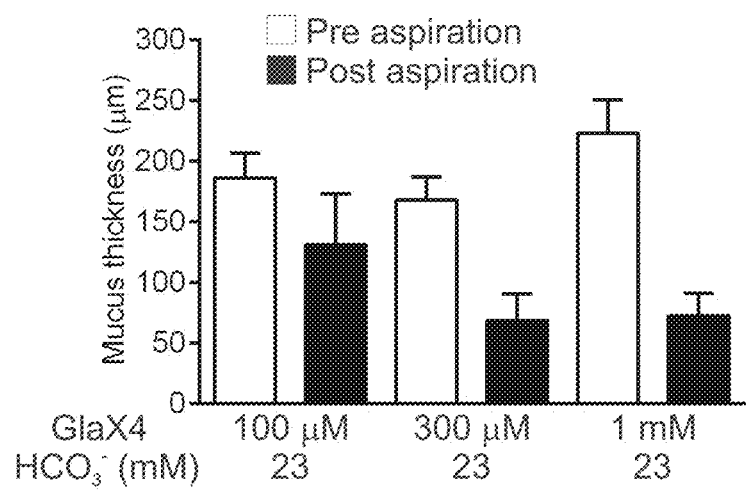
FIGS. 4A and 4B are graphs demonstrating mucus detachment effect of the Gla-peptide with four units (GlaX4) In the CF mouse ileum.
Figure 4B:
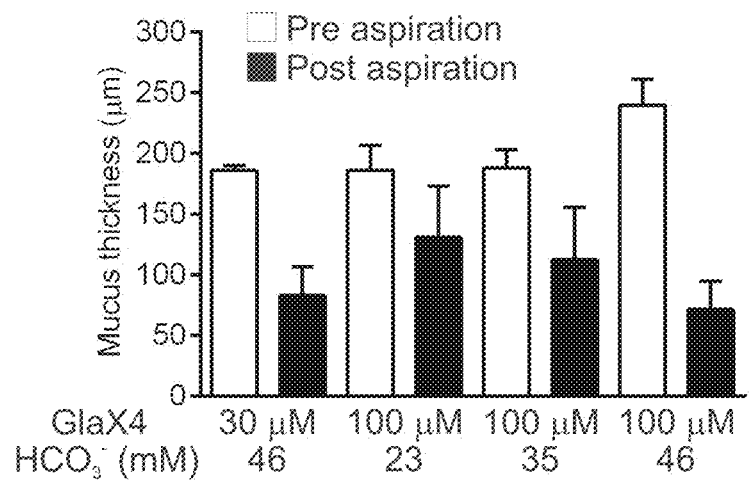

FIG. 4: In the CF mouse ileum, the Gla-peptide with four units (GlaX4) was effective at detaching the mucus. A. Explants from CF mouse ileum mounted in the horizontal Ussing-type chamber were incubated for 60 min with different concentrations of the GlaX4 peptide and mucus was measured before (Pre, white bars) and after aspiration (Post, black bars). More mucus could be aspirated with 300 µM than with 100 µM, but the thickness of the remaining mucus was similar with 1 mM as with 300 µM, indicating that the maximal effect may be reached already at 300 µM. Mucus attachment is normalized with 300 µM GlaX4. B. In combination with increased concentrations of bicarbonate (35 and 46 mM), the effect was improved compared to 4-mer alone. Incubation with a combination of 30 µM 4-mer and 46 mM bicarbonate gave a better effect (less remaining mucus) than 100 µM 4-mer alone. Mucus attachment was normalized with 100 µM 4-mer in combination with 46 mM bicarbonate.

Figure 5:
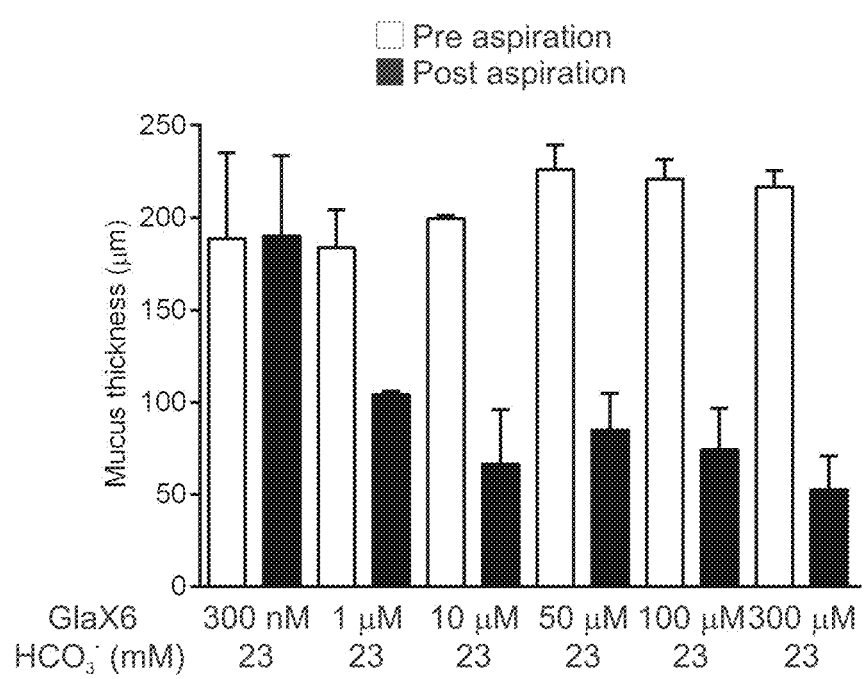
FIG. 5 is a graph demonstrating potent mucus detaching properties of the Gla-peptide with six units (GlaX6) in the CF mouse ileum.

FIG. 5: In the CF mouse ileum, the Gla-peptide with six units (GlaX6) had potent mucus detaching properties. Explants from CF mouse ileum mounted in the horizontal Ussing-type chamber were incubated for 60 min with different concentrations of the GlaX6 peptide and mucus was measured before (Pre, white bars) and after aspiration (Post, black bars). The lowest concentration tested, 300 nM, was without detaching effect, but the mucus detaching effect was evident already at 1 µM. The thickness of the remaining mucus was similar with 10 µM as with 50, 100 and 300 µM, indicating that the maximal effect may be reached already at 10 or 50 µM. Mucus attachment is normalized with as low as 10 µM GlaX6.

Figure 6A:
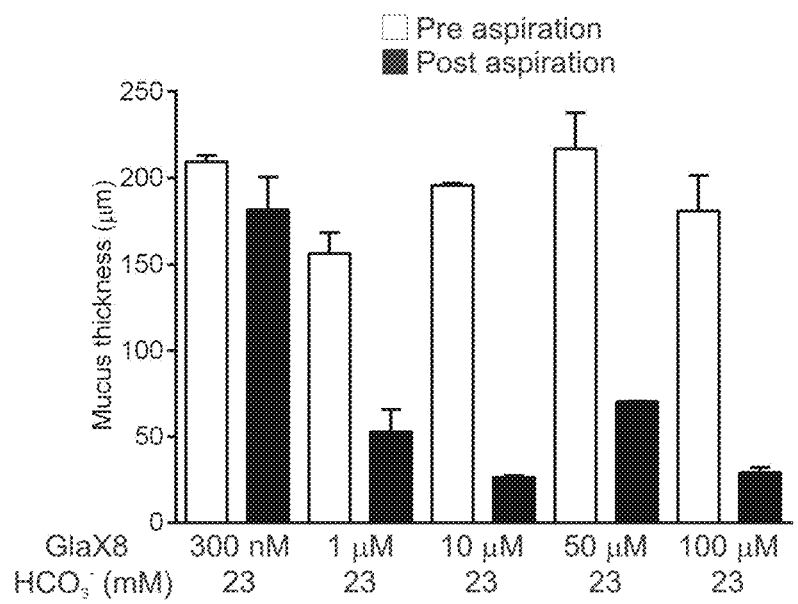
FIGS. 6A and 6B are graphs demonstrating potent mucus detaching properties of the Gla-peptide with eight units (GlaX8) in the CF mouse ileum. Doubling the amount of bicarbonate increases the effect of GlaX8.
Figure 6B:
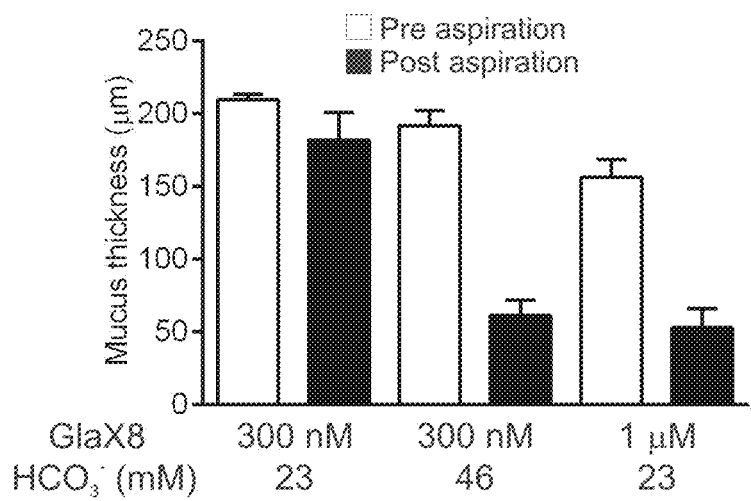

FIG. 6: In the CF mouse ileum, the Gla-peptide with eight units (GlaX8) had potent mucus detaching properties. A. Explants from CF mouse ileum mounted in the horizontal Ussing-type chamber were incubated for 60 min with different concentrations of the GlaX8 peptide and mucus was measured before (Pre, white bars) and after aspiration (Post, black bars) at a normal bicarbonate concentration of 23 mM. The lowest concentration tested, 300 nM, had some small mucus detaching effect and at 1 µM the mucus attachment was normalized. The thickness of the remaining mucus was similar with 1, 10, 50 and 100 µM, indicating that the maximal effect may be reached already at 1 or 10 µM. B. Explants from CF mouse ileum mounted in the horizontal Ussing-type chamber were incubated for 60 min with different concentrations of the GlaX8 peptide and mucus was measured before (Pre, white bars) and after aspiration (Post, black bars) with 23 or 46 mM bicarbonate as in A. The 8-mer at 300 nM had some small effect on CF mucus attachment at 23 mM bicarbonate, but in combination with 46 mM bicarbonate, the mucus attachment was normalized. The thickness of the remaining mucus was similar with 300 nM 8-mer in combination with 46 mM bicarbonate as with 1 µM 8-mer alone.

Figure 7:
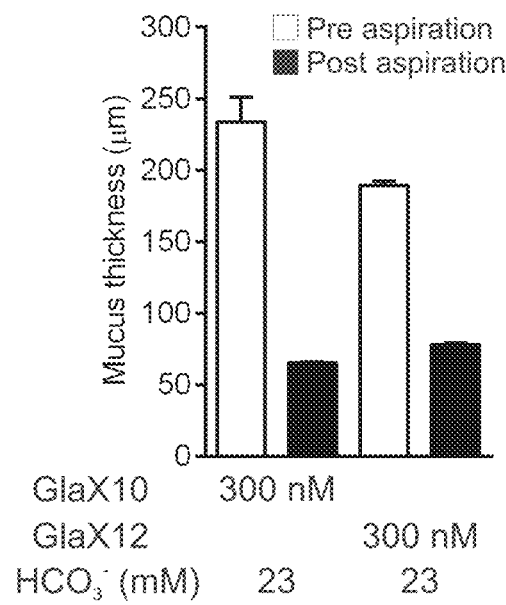
FIG. 7 is a graph demonstrating potent mucus detaching properties of the Gla-peptide with ten and twelve units (GlaX10 and GlaX12) in the CF mouse ileum.

FIG. 7: In the CF mouse ileum, the Gla-peptide with ten and twelve units (GlaX10 and GlaX12) had very potent mucus detaching properties. Explants from CF mouse ileum mounted in the horizontal Ussing-type chamber were incubated for 60 min with different concentrations of the GlaX10 or GlaX12 peptide and mucus was measured before (Pre, white bars) and after aspiration (Post, black bars). The mucus attachment was normalized already at 300 nM with both the 10-mer and the 12-mer.

Figure 8:
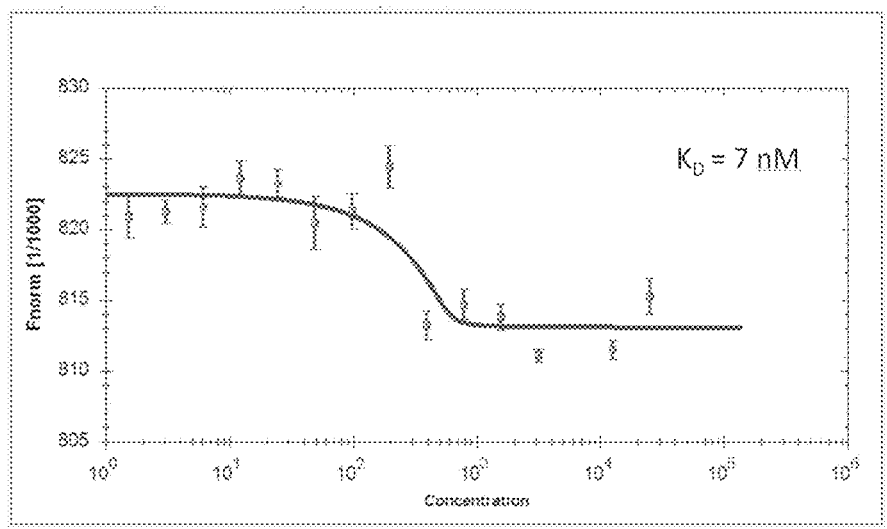
FIG. 8 is a graph showing that the GlaX8 peptide can displace calcium from the MUC2 mucin N-terminus at low nanomolar concentrations.

FIG. 8: The GlaX8 peptide can displace calcium from the MUC2 mucin N-terminus at low nanomolar concentrations. GFP-labeled MUC2 N-terminus (590 nM) and calcium (400 µM) was titrated from 1.5 nM to 50 µM GlaX8 at pH 5.5. At low levels of GlaX8, the amount of free calcium caused aggregation of MUC2, whereas higher levels of GlaX8 could compete out calcium from MUC2 shown as higher mobility. The apparent equilibrium constant was 7 nM.

Figure 9:
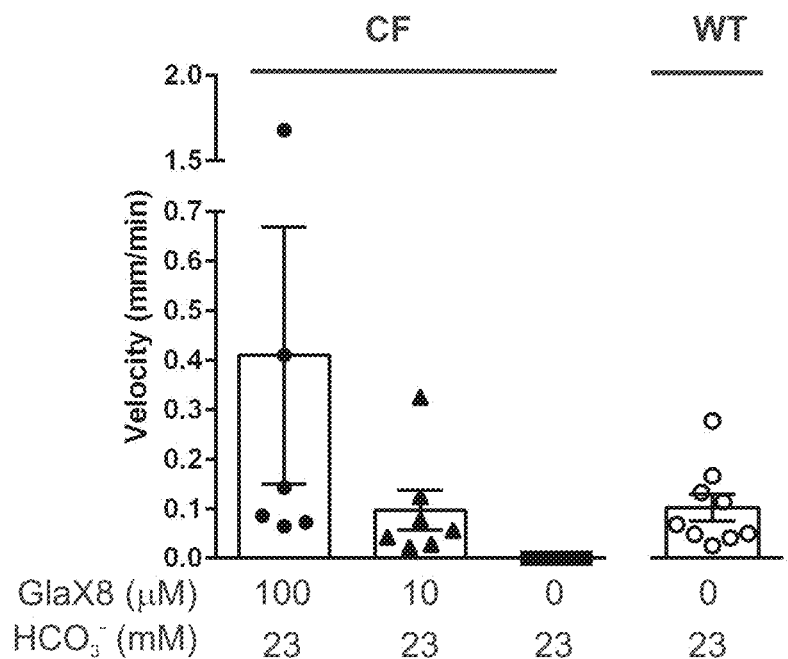
FIG. 9 is a graph showing that the GlaX8 normalizes and increases mucus strand transport velocity in CF piglet trachea where the the mucus is not transported at all without this treatment.

FIG. 9: The GlaX8 peptide increases mucus strand transport speed in CF piglet trachea. Normal and CF trachea-bronchi from newborn piglets were mounted and the mucus strands stained by Alcian blue. The transport of the mucus stands by the cilia was recorded by a video microscope and the velocity determined. In the normal (WT, wild type) piglet the transport speed was estimated to 0.1-0.2 mm/min. In the CF piglet there was no movement of the mucus at all (GlaX8=0). When the tissue was incubated with 10 or 100 µM GlaX8 for 5 min, the transport velocity of Alcian blue stained mucus strands was increased. The lower concentration reaching normal velocities, whereas 100 µM GlaX8 restored the mucus transport to normal levels or in some measurements even higher. The effect was sustained for at least one hour.

FIG. 10: Principle of mucus thickness measurement in the ileum. A. Initial mucus thickness was measured from the added charcoal particles on the mucus to the villi tips (pre in FIG. 5A). B. In order to establish total mucus thickness, all mucus was removed, new charcoal and Krebs-mannitol were added to the chamber and villus height was measured from charcoal to villus tip. After this removal, the mucus

19 thickness was measured again from the charcoal particles to the villi tips (post in FIG. 5A). The total mucus thickness preaspiration and postaspiration were calculated. In FIG. 10, reference numerals denote the following: 1: Crypt; 2: Villus; 3: Mucus pre aspiration; 4: Mucus post aspiration; 5: Black dots represent charcoal particles, indicating the level of mucus.

FIG. 11: Newborn piglet airway mounted in the experiment chamber. The Sylgard coated chamber was placed in a heating block and kept at 37° C. during the experiment. The Petri dish is 4 cm in diameter.

Summary of Experimental Results and Findings

- Peptides of gamma-carboxy glutamic acid bind calcium with high affinity.
- Longer peptides binds with higher affinity.
- Gamma-carboxy glutamic acid with 8 residues binds calcium in low nanomolar concentrations.
- The N-terminal part of gel-forming mucins binds calcium in low micromolar concentrations at the pH found in cellular storage granulae.
- The gamma-carboxy glutamic acid peptide with eight residues were able to compete out calcium from the mucin at low micromolar concentration.
- Both the intestinal and trachea-bronchial tissue integrity and viability was unaffected by incubation with gamma-carboxy glutamic acid peptides.
- Gamma-carboxy glutamic acid peptides trigger detachment of abnormal and attached cystic fibrosis mucus.
- Sodium bicarbonate potentiate the effect of gamma-carboxy glutamic acid peptides.
- Mucus strands in normal pig trachea are transported by cilia, but is attached an not moving in cystic fibrosis pigs.
- Gamma-carboxy glutamic acid peptides detach the mucus and allow the mucus strands to move in cystic fibrosis pig trachea.

Together, the results of the extensive experimentation underlying the present invention provide far-reaching evidence for the use of pharmaceutical compounds based on gamma-carboxy glutamic acid and related calcium binding compounds in the treatment of diseases related to stagnated mucus in upper and lower respiratory tracts.

Itemized List of Embodiments

1. A compound capable of binding calcium ions, said compound comprising at least two gamma-carboxy glutamate units, wherein each gamma-carboxy glutamate unit is defined by Formula 1

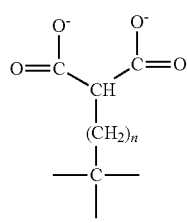

Formula 1 wherein n is 0, 1, 2, 3, 4, 5, 6, 7, 8, 9 or 10;
for use in the treatment and/or prevention of a disorder characterized by mucus stagnation in the upper and/or lower respiratory tract.

2. Compound capable of binding calcium ions for use according to item 1, wherein said compound comprises a linker between at least two gamma-carboxy glutamate units, which linker is selected from Formula A, B, C, D, E and F:

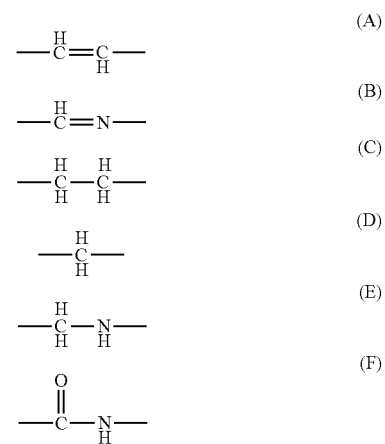

3. Compound capable of binding calcium ions for use according to item 1, wherein said compound comprises a linker between at least two gamma-carboxy glutamate units, wherein said linker is a peptide bond according to formula 2:

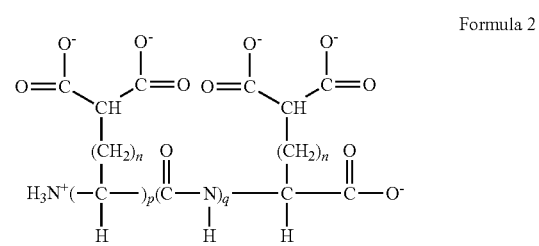

Formula 2 wherein
n is 0, 1, 2, 3, 4, 5, 6, 7, 8, 9, or 10, such as 1;
q and p are equal; and
each of p, q is 1, 2, 3, 4, 5, 6, 7, 8, 9, 10, 11, 12, 13, 14, 15, 16, 17, 19, or 20.

4. Compound capable of binding calcium ions for use according to item 1, wherein said compound comprises at least two gamma-carboxy glutamate units according to Formula 3:

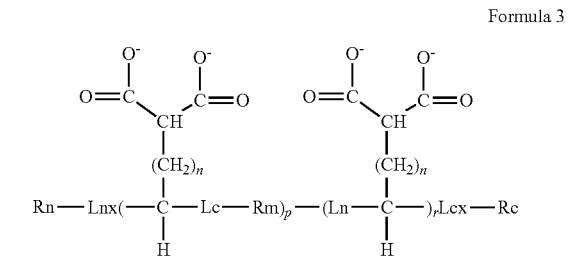

Formula 3 wherein
n is 0 or an integer 1-10, such as 0, 1, 2, 3, 4, 5, 6, 7, 8, 9, or 10, such as from 1 to 5, such as 1;

p is an integer 1-20; such as 1, 2, 3, 4, 5, 6, 7, 8, 9, 10, 11, 12, 13, 14, 15, 16, 17, 19, or 20; for example 2-11, such as 4-11;

r is an integer 1-20, such as 1, 2, 3, 4, 5, 6, 7, 8, 9, 10, 11, 12, 13, 14, 15, 16, 17, 19, or 20;

under proviso that p+r equals 3, 4, 5, 6, 7, 8, 9, 10, 11, 12, 13, 14, 15, 16, 17, 19, or 20, and typically p+r equals 5, 6, 7, 8, 9, 10, 11 or 12;

wherein each of Rn, Rm, Rc, Lc, Ln, Lcx, and Lnx is independently present or absent, and where present, Ln is independently selected from: —NH—; and any one of formula (A)-(F):

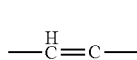 (A)

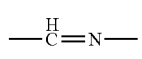 (B)

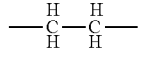 (C)

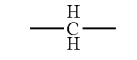 (D)

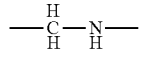 (E)

 (F)

Lc is independently selected from:
—CO—; and
any one of formula (A)-(F) above;
or, provided Rm is absent, Ln and Lc together forms a linker according to any one of formula (A)-(F);

Lnx is —NH—;
Lcx is —CO—;

Rn is independently selected from: $-H_2^+$; $-CH_3$; 1-20 repetitions of any naturally occurring amino acid; Ser substituted with mono- or oligosaccharide; Thr substituted with mono- or oligosaccharide; and a hydrocarbon chain with up to five carbon atoms.

Rm is independently selected from —$CH_2$—; 1-20 repetitions of any amino acid; Ser substituted with mono- or oligosaccharide; Thr substituted with mono- or oligosaccharide; and a hydrocarbon chain having up to 5 carbon atoms; and Rc is independently selected from —$O^-$; —$CH_3$; 1-20 repetitions of any naturally occurring amino acid; Ser substituted with mono- or oligosaccharide; Thr substituted with mono- or oligosaccharide; and a hydrocarbon chain with up to five carbons.

5. Compound capable of binding calcium ions for use according to item 4,
where Rm is independently selected from:
—$CH_2$—;
Ser substituted with mono- or oligosaccharide;
Thr substituted with mono- or oligosaccharide; and
a hydrocarbon chain having up to 5 carbon atoms.

6. Compound capable of binding calcium ions for use according to item 4, wherein Rn is —$H_2^+$ and/or Rc is —$O^-$.

7. Compound capable of binding calcium ions for use according to item 4, wherein at least one Rm is absent, such as wherein all Rm are absent.

8. Compound capable of binding calcium ions for use according to any item 1 or 2, comprising 2-20 gamma-carboxy glutamate units, such as 3-12 gamma-carboxy glutamate units, such as 5-10 gamma-carboxy glutamate units, such as 6-8 gamma-carboxy glutamate units, such as 8 gamma-carboxy glutamate units.

9. Compound capable of binding calcium ions for use according to any one of items 2-7, wherein p is an integer from 1 to 19, such as an integer from 2 to 11, such as an integer from 4 to 9, such as an integer from 5 to 7, such as 7.

10. Compound capable of binding calcium ions for use according to any one of items 4-8, wherein in Formula 3, Rn is —$H_2^+$, Rm is absent, Rc is —$O^-$, n=1 and p is selected from the group consisting 1, 3, 5, 7, 9 and 11.

11. Compound capable of binding calcium ions for use according item 4, wherein said compound is a compound according to Formula 3, wherein Rn is —$H_2^+$, all Rm are absent, Rc is —$O^-$, n=1 and p=7.

12. Compound capable of binding calcium ions for use according to any one of items 1-11, which is capable of binding to $Ca^{2+}$ such that the $K_D$ value of the interaction is at least $1\times10^{-8}$ M at pH 7.3.

13. Compound capable of binding calcium ions for use according to any one of items 1-12, wherein said disorder is a respiratory disease or nasal disease, such as a respiratory disease or nasal disease selected from the group consisting of acute rhinitis; chronic rhinitis; sinuitis; acute bronchitis; chronic bronchitis; chronic obstructive pulmonary disease (COPD); emphysema; bronchiectasis; respiratory inflammatory or allergic disease, such as a systemic inflammatory disease associated with respiratory mucus stagnation and mucus overproduction; asthma; cystic fibrosis; and bacterial infection.

14. Compound capable of binding calcium ions for use according to item 13, wherein said respiratory disease is selected from the group consisting of acute rhinitis, chronic rhinitis, sinuitis, acute bronchitis, chronic bronchitis, chronic obstructive pulmonary disease (COPD), emphysema, and bronchiectasis.

15. Compound capable of binding calcium ions for use according to item 13, wherein said respiratory disease is a respiratory inflammatory or allergic disease, such as a systemic inflammatory disease associated with respiratory mucus stagnation and mucus overproduction.

16. Compound capable of binding calcium ions for use according to item 13, wherein said respiratory disease is asthma.

17. Compound capable of binding calcium ions for use according to item 13, wherein said respiratory disease is cystic fibrosis.

18. Compound capable of binding calcium ions for use according to item 13, wherein said respiratory disease or nasal disease is a bacterial infection.

19. A compound capable of binding calcium ions, defined according to Formula 3:

Formula 3

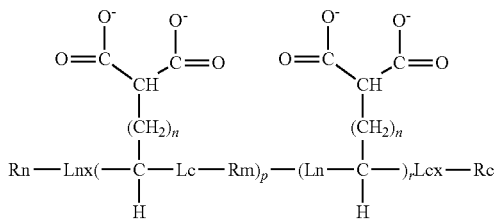

wherein
- n is 0 or an integer 1-10, such as 0, 1, 2, 3, 4, 5, 6, 7, 8, 9, or 10, such as from 1 to 5, such as 1;
- p is an integer 1-20; such as 1, 2, 3, 4, 5, 6, 7, 8, 9, 10, 11, 12, 13, 14, 15, 16, 17, 19, or 20; for example 2-11, such as 4-11;
- r is an integer 1-20, such as 1, 2, 3, 4, 5, 6, 7, 8, 9, 10, 11, 12, 13, 14, 15, 16, 17, 19, or 20;
- under proviso that p+r equals 3, 4, 5, 6, 7, 8, 9, 10, 11, 12, 13, 14, 15, 16, 17, 19, or 20, and typically p+r equals 5, 6, 7, 8, 9, 10, 11 or 12;
- wherein each of Rn, Rm, Rc, Lc, Ln, Lcx, and Lnx is independently present or absent, and where present,
- Ln is independently selected from: —NH—; and any one of formula (A)-(F):

(A) 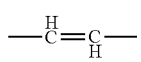

(B) 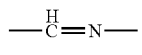

(C) 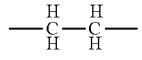

(D) 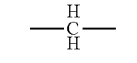

(E) 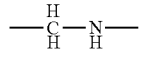

(F)

$$-\underset{}{\overset{O}{\underset{}{C}}}-\underset{H}{N}-$$

Lc is independently selected from: —CO—; and any one of formula (A)-(F) above;
or, provided Rm is absent, Ln and Lc together forms a linker according to any one of formula (A)-(F);
Lnx is —NH—;
Lcx is —CO—;
Rn is independently selected from: —$H_2^+$; —$CH_3$; 1-20 repetitions of any naturally occurring amino acid; Ser substituted with mono- or oligosaccharide; Thr substituted with mono- or oligosaccharide; and a hydrocarbon chain with up to five carbon atoms.
Rm is independently selected from —$CH_2$—; 1-20 repetitions of any amino acid; Ser substituted with mono- or oligosaccharide; Thr substituted with mono- or oligosaccharide; and a hydrocarbon chain having up to 5 carbon atoms; and
Rc is independently selected from —$O^-$; —$CH_3$; 1-20 repetitions of any naturally occurring amino acid; Ser substituted with mono- or oligosaccharide; Thr substituted with mono- or oligosaccharide; and a hydrocarbon chain with up to five carbons.

20. Compound capable of binding calcium ions according to item 19, wherein n is 0, 2, 3, 4, 5, 6, 7, 8, 9 or 10.
21. Compound capable of binding calcium ions according to item 19, where Rm is independently selected from —$CH_2$—;
    Ser substituted with mono- or oligosaccharide;
    Thr substituted with mono- or oligosaccharide; and
    a hydrocarbon chain having up to 5 carbon atoms.
22. Compound capable of binding calcium ions according to item 19, wherein Rn is —$H_2^+$ and/or Rc is —$O^-$.
23. Compound capable of binding calcium ions according to any one of items 19-22, wherein at least one Rm is absent, such as wherein all Rm are absent.
24. Compound capable of binding calcium ions according to any one of items 19-23, wherein p is an integer from 1 to 19, such as an integer from 2 to 11, such as an integer from 4 to 9, such as an integer from 5 to 7, such as 7.
25. Compound capable of binding calcium ions according to any one of items 19-24, wherein in Formula 3, Rn is —$H_2^+$, Rm is absent, Rc is —$O^-$, n=1 and p is selected from the group consisting 1, 3, 5, 7, 9 and 11.
26. Compound capable of binding calcium ions for use according to item 19, wherein said compound is a compound according to Formula 3, wherein Rn is —$H_2^+$, all Rm are absent, Rc is —$O^-$, n=1 and p=7.
27. Compound capable of binding calcium ions for use according to any one of items 19-26, which is capable of binding to $Ca^{2+}$ such that the $K_D$ value of the interaction is at least $1 \times 10^{-8}$ M at pH 7.3.
28. A compound capable of binding calcium ions comprising at least two gamma-carboxy glutamate units each being defined according to Formula 1:

Formula 1

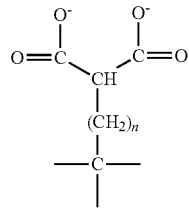

wherein n is 0, 1, 2, 3, 4, 5, 6, 7, 8, 9 or 10;
said compound further comprising a linker between at least two gamma-carboxy glutamate units, which linker is selected from any one of formula A-E:

(A) 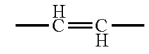

(B) 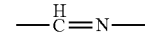

(C) 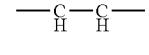

(D) 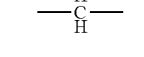

(E) 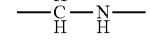

29. Compound capable of binding calcium ions according to any one of items 19-28, for use as a medicament.
30. Compound capable of binding calcium ions according to item 29, for use in the treatment and/or prevention of a disorder characterized by mucus stagnation in the upper and/or lower respiratory tract, such as a disorder defined in any one of items 13-18.
31. A pharmaceutical composition comprising a therapeutically effective amount of a compound capable of binding calcium ions as defined in any one of items 19-28 and a pharmaceutically acceptable carrier and/or excipient.
32. Pharmaceutical composition according to item 31, comprising a pharmaceutically acceptable salt, such as a salt selected from the group consisting of salts derived from inorganic bases, such as pharmaceutically acceptable salts of ammonium, potassium, sodium salts, salts derived from pharmaceutically acceptable organic, non-toxic bases such as salts of primary, secondary, and tertiary amines, substituted amines including naturally occurring substituted amines, cyclic amines, isopropylamine, trimethyl amine, diethylamine, triethylamine, tripropylamine, ethanolamine, 2-dimethylaminoethanol, 2-diethylaminoethanol, trimethamine, dicyclohexylamine, and the free amino acids lysine, arginine, and histidine; and any combination thereof.
33. Pharmaceutical composition according to item 31 or 32, further comprising a pharmaceutically acceptable preservative, such as a preservative selected from the group consisting of antibacterial agents, antifungal agents, ethanol, propylene glycol, benzyl alcohol, chlorobutanol, quaternary ammonium salts such as cetylypridinium chloride and benzalkonium chloride, parabens such as methyl paraben, ethyl paraben and propyl paraben, chlorhexidine, benzoic acid and the salts thereof, parahydroxybenzoic acids and the salts thereof, alkyl esters of parahydroxybenzoic acid and the salts thereof, nitrate, chloride, acetate, and borate, or antioxidants; and any combination thereof.
34. Pharmaceutical composition according to any one of items 31-33, further comprising a pharmaceutically acceptable pH adjusting agent or buffer, such as an agent selected from citric acid, sodium citrate, sodium bicarbonate, tris dibasic sodium phosphate, magnesium oxide, calcium carbonate and magnesium hydroxide, or a buffer selected from bicarbonate buffer, acetate buffers, citrate buffers, phosphate buffers, lactic acid buffers, tris buffer, and borate buffers, and any combination thereof.
35. Pharmaceutical composition according to any one of items 31-34, having a pH-value in the range of from 7 to 10.
36. Pharmaceutical composition according to any one of items 31-35, further comprising $HCO_3^-$ at a concentration in the range of 0-120 mM, such as 20-120 mM.
37. Pharmaceutical composition according to item 36, wherein said $HCO_3^-$ is present at a concentration in the range of up to 70 mM.
38. Pharmaceutical composition according to item 37, wherein said $HCO_3^-$ is present at a concentration in the range of 20-25 mM, such as 23 mM.
39. Pharmaceutical composition according to item 37, wherein said $HCO_3^-$ is present at a concentration in the range of 45-50 mM, such as 46 mM.
40. Pharmaceutical composition according to any one of items 31-39, further comprising an additional therapeutically active agent.
41. Pharmaceutical composition according to item 40, further comprising hypertonic saline at a concentration of up to 7% by weight.
42. Pharmaceutical composition according to any one of items 31-41, further comprising at least one osmotically active agent, such as at least one osmotically active agent selected from the group consisting of mono-, di-tri-, tetra-, penta-, and oligosaccharides, glycitols such as sorbitol and mannitol, and other non-fermentable sugars, and any combination thereof.
43. Pharmaceutical composition according to any one of items 31-42, wherein said composition is formulated for nasal and/or tracheal-bronchial administration.
44. Pharmaceutical composition according to item 43, wherein said composition is formulated as a liquid, a mist or a dry powder.
45. Pharmaceutical composition according to item 44, wherein said composition is formulated as a dry powder and wherein the concentration recited in any one of items 31-44 correspond to the concentration based on a solution of said dry powder having solution volume of 10 ml.
46. A method of treatment and/or prevention of a disorder characterized by mucus stagnation in the upper and/or lower respiratory tract, comprising administering to a patient in need thereof a therapeutically effective amount of a compound capable of binding calcium ions comprising gamma-carboxy glutamate units, as defined according to any one of items 1-28.
47. Method of treatment and/or prevention according to item 46, wherein said disorder is a respiratory disease or nasal disease, such as a disease defined in any one of items 13-18.
48. Method of treatment and/or prevention of a disorder characterized by mucus stagnation in the upper and/or lower respiratory tract according to any one of items 46-47, wherein administration is nasal and/or tracheal-bronchial administration.
49. Method of treatment and/or prevention of a disorder characterized by mucus stagnation in the upper and/or lower respiratory tract according to item 48, wherein said administration is administration using a liquid, a mist or a dry powder.
50. Method of treatment and/or prevention of a disorder characterized by mucus stagnation in the upper and/or lower respiratory tract according to any one of items 46-49, further comprising simultaneous and/or concomitant co-administration of at least one additional therapeutic agent selected from hypertonic saline solution at a concentration of 7% by weight; osmotically active agents, such as an osmotically active agent selected from the group consisting of mono-, di-tri-, tetra-, penta-, and oligosaccharides; glycitols such as sorbitol and mannitol, and non-fermentable sugars, and any combination thereof.
51. Method of treatment and/or prevention of a disorder characterized by mucus stagnation in the upper and/or lower respiratory tract according to any one of items 46-50, wherein said administration is 1-20 times per day, such as 3-10 times per day.
52. Method of treatment and/or prevention of a disorder characterized by mucus stagnation in the upper and/or lower respiratory tract according to any one of items 46-51, wherein said administration achieves a local concentration of said compound of from 1 nm to 10 mM, such as from 10 nM to 5 mM, such as from 100 nM to 1 mM, such as from 100 nM to 100 μM.

53. Use of a calcium binding compound as defined in any one of items 1-43 in the manufacture of a medicament.
54. Use of a calcium binding compound as defined in any one of items 1-43 in the manufacture of a medicament for the treatment of a disorder characterized by mucus stagnation in the upper and/or lower respiratory tract.
55. Use according to item 54, wherein the disorder is as defined in any one of items 13-18.
56. A compound for use according to any one of the items 1-18, wherein said use provides a local concentration of said compound, at the apical side of the epithelium, of from 1 nm to 10 mM, such as from 10 nM to 5 mM, such as from 100 nM to 1 mM, such as from 100 nM to 100 μM.

The person skilled in the art realizes that the present invention by no means is limited to the preferred embodiments described above. On the contrary, many modifications and variations are possible within the scope of the appended claims. Variations to the disclosed embodiments can be understood and effected by the skilled person in practicing the claimed invention, from a study of the drawings, the disclosure, and the appended claims.

In the claims and in the itemized list of embodiments above, the word "comprising" does not exclude other elements or steps, and the indefinite article "a" or "an" does not exclude a plurality. The mere fact that certain measures are recited in mutually different dependent claims does not indicate that a combination of these measured cannot be used to advantage.

What is claimed is:

1. A method of treatment of a disorder characterized by mucus stagnation in the upper and/or lower respiratory tract, comprising administering to a patient in need thereof a therapeutically effective amount of a compound capable of binding calcium ions, which compound is defined according to Formula 3:

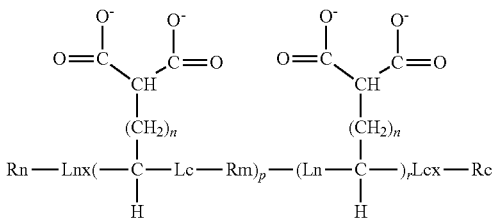

Formula 3 wherein
n is 0 or an integer 1-10;
p is an integer 1-20;
r is an integer 1-20;
with the proviso that p+r equals from 3 to 20;
each of Rn, Rm, Rc, Lc, Ln, Lcx, and Lnx is independently present or absent, and
where present, Ln is independently selected from the group consisting of —NH—; and any one of formula (A)-(F):

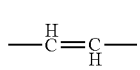  (A)

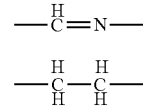  (B)

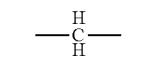  (C)

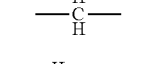  (D)

(E)

(F)

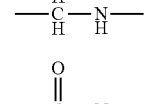

Lc is independently selected from the group consisting of —CO—; and any one of formula (A)-(F) above;
or,
provided Rm is absent, Ln and Lc together form a linker according to any one of formula (A)-(F); Lnx is —NH—;

Lcx is —CO—;

Rn is independently selected from the group consisting of —H$_{2+}$; —CH$_3$; 1-20 repetitions of any naturally occurring amino acid; Ser substituted with mono- or oligosaccharide; Thr substituted with mono- or oligosaccharide; and a hydrocarbon chain with up to five carbon atoms;

Rm is independently selected from the group consisting of —CH$_2$—; 1-20 repetitions of any amino acid; Ser substituted with mono- or oligosaccharide; Thr substituted with mono- or oligosaccharide; and a hydrocarbon chain having up to 5 carbon atoms; and Rc is independently selected from the group consisting of —O—; —CH$_3$; 1-20 repetitions of any naturally occurring amino acid; Ser substituted with mono- or oligosaccharide; Thr substituted with mono- or oligosaccharide; and a hydrocarbon chain with up to five carbons.

2. The method of treatment according to claim 1, wherein said disorder is a respiratory disease or nasal disease selected from the group consisting of acute rhinitis; chronic rhinitis; sinuitis; acute bronchitis; chronic bronchitis; chronic obstructive pulmonary disease (COPD); emphysema; bronchiectasis; a systemic inflammatory disease associated with respiratory mucus stagnation and mucus overproduction; asthma; cystic fibrosis; and bacterial infection.

3. The method of treatment according to claim 2, wherein said respiratory disease is cystic fibrosis.

4. The method of treatment according to claim 1, wherein said administration is nasal and/or tracheal-bronchial administration.

5. The method of treatment of a disorder according to claim 1, wherein said administration is administration using a liquid, a mist or a dry powder.

6. The method of treatment of a disorder according to claim 1, further comprising simultaneous and/or concomitant co-administration of at least one additional therapeutic agent selected from hypertonic saline solution at a concentration of 7% by weight; osmotically active agents; glycitols such as sorbitol and mannitol, and non-fermentable sugars.

7. The method of treatment of a disorder according to claim 1, wherein said administration achieves a local concentration of said compound at the apical side of the epithelium of from 1 nM to 10 mM.

8. The method of treatment of a disorder according to claim 1, wherein said administration is 1-20 times per day.

* * * * *